United States Patent
Hayashi et al.

(10) Patent No.: US 9,273,000 B2
(45) Date of Patent: Mar. 1, 2016

(54) METHOD FOR PRODUCING ORGANIC ELECTROLUMINESCENCE ELEMENT

(75) Inventors: Naoyuki Hayashi, Ashigarakami-gun (JP); Ikuo Kinoshita, Ashigarakami-gun (JP)

(73) Assignee: UDC Ireland, Dublin (IE)

( * ) Notice: Subject to any disclaimer, the term of this patent is extended or adjusted under 35 U.S.C. 154(b) by 248 days.

(21) Appl. No.: 13/634,774

(22) PCT Filed: Mar. 2, 2011

(86) PCT No.: PCT/JP2011/054740
§ 371 (c)(1),
(2), (4) Date: Sep. 13, 2012

(87) PCT Pub. No.: WO2011/114886
PCT Pub. Date: Sep. 22, 2011

(65) Prior Publication Data
US 2013/0011952 A1    Jan. 10, 2013

(30) Foreign Application Priority Data

Mar. 15, 2010    (JP) ................................. 2010-057556

(51) Int. Cl.
*H01L 51/50* (2006.01)
*C07D 209/86* (2006.01)
(Continued)

(52) U.S. Cl.
CPC ............ *C07D 209/86* (2013.01); *C07D 235/18* (2013.01); *C07D 403/10* (2013.01);
(Continued)

(58) Field of Classification Search
CPC ............ H01L 51/0003; H01L 51/0005; H01L 51/0006; H01L 51/0026; H01L 51/56; H01L 51/5012; H01L 51/0085
USPC ...................................................... 438/22, 99
See application file for complete search history.

(56) References Cited

U.S. PATENT DOCUMENTS 6,001,413 A * 12/1999 Matsuura et al. ............... 427/64
2004/0229080 A1    11/2004 Ikeda
(Continued)

FOREIGN PATENT DOCUMENTS

| CN | 101094904 | 12/2007 |
|----|-----------|---------|
| JP | 06-330034 A | 11/1994 |

(Continued)

OTHER PUBLICATIONS

English machine translation of JP2007-123392 as retrieved from J-PlatPat (online Japanese Platform for Patent Information) on Sep. 30, 2015.

*Primary Examiner* — Savitr Mulpuri
(74) *Attorney, Agent, or Firm* — Riverside Law LLP

(57) ABSTRACT

Provided is a method for producing an organic electroluminescence device which contains an anode, a cathode and an organic layer between the anode and the cathode where the organic layer contains a light-emitting layer and an adjacent layer adjacent to the light-emitting layer, the method including: applying to the adjacent layer a coating liquid prepared by dissolving or dispersing a light-emitting material and a host material in a solvent, and heating the coating liquid applied to the adjacent layer at a temperature higher than a melting temperature of the host material and higher than a boiling point of the solvent, to thereby form the light-emitting layer, wherein a difference as an absolute value between contact angle A (°) of the light-emitting layer with respect to pure water and contact angle B (°) of the adjacent layer with respect to pure water is 13 (°) or smaller.

6 Claims, 1 Drawing Sheet

(51) Int. Cl.
*H01L 51/00* (2006.01)
*C07D 235/18* (2006.01)
*C07D 403/10* (2006.01)
*C07D 403/14* (2006.01)
*C09K 11/06* (2006.01)
*H05B 33/10* (2006.01)
*H05B 33/20* (2006.01)
*H05B 33/14* (2006.01)
*H01L 51/56* (2006.01)

(52) U.S. Cl.
CPC ............. *C07D403/14* (2013.01); *C09K 11/06* (2013.01); *H01L 51/0003* (2013.01); *H01L 51/0005* (2013.01); *H01L 51/0026* (2013.01); *H01L 51/0072* (2013.01); *H01L 51/5012* (2013.01); *H01L 51/5016* (2013.01); *H05B 33/10* (2013.01); *H05B 33/14* (2013.01); *H05B 33/20* (2013.01); *C09K 2211/1029* (2013.01); *C09K 2211/1044* (2013.01); *H01L 51/006* (2013.01); *H01L 51/0081* (2013.01); *H01L 51/0085* (2013.01); *H01L 51/56* (2013.01); *H01L 2251/556* (2013.01)

(56) References Cited

U.S. PATENT DOCUMENTS

| | | | |
|---|---|---|---|
| 2005/0276910 A1 | 12/2005 | Gupta | |
| 2006/0160456 A1 | 7/2006 | Ikeda | |
| 2007/0009759 A1* | 1/2007 | Burn et al. | 428/690 |
| 2009/0115310 A1* | 5/2009 | Yamamoto | 313/498 |
| 2009/0322217 A1* | 12/2009 | Inoue et al. | 313/504 |
| 2010/0155760 A1* | 6/2010 | Lee et al. | 257/98 |
| 2010/0171101 A1* | 7/2010 | Tanaka et al. | 257/40 |
| 2010/0171418 A1* | 7/2010 | Kinoshita et al. | 313/504 |
| 2010/0231123 A1* | 9/2010 | Otsu et al. | 313/504 |
| 2011/0253990 A1* | 10/2011 | Ishikawa et al. | 257/40 |
| 2011/0272687 A1* | 11/2011 | Katakura et al. | 257/40 |

FOREIGN PATENT DOCUMENTS

| | | |
|---|---|---|
| JP | 2006-278005 A | 10/2006 |
| JP | 2007-123392 A | 5/2007 |
| JP | 2008-226642 A | 9/2008 |
| JP | 2009-129567 A1 | 6/2009 |
| JP | 2009-163889 A | 7/2009 |
| JP | 2011-051918 A | 3/2011 |
| WO | 2004/064453 A1 | 7/2004 |

* cited by examiner

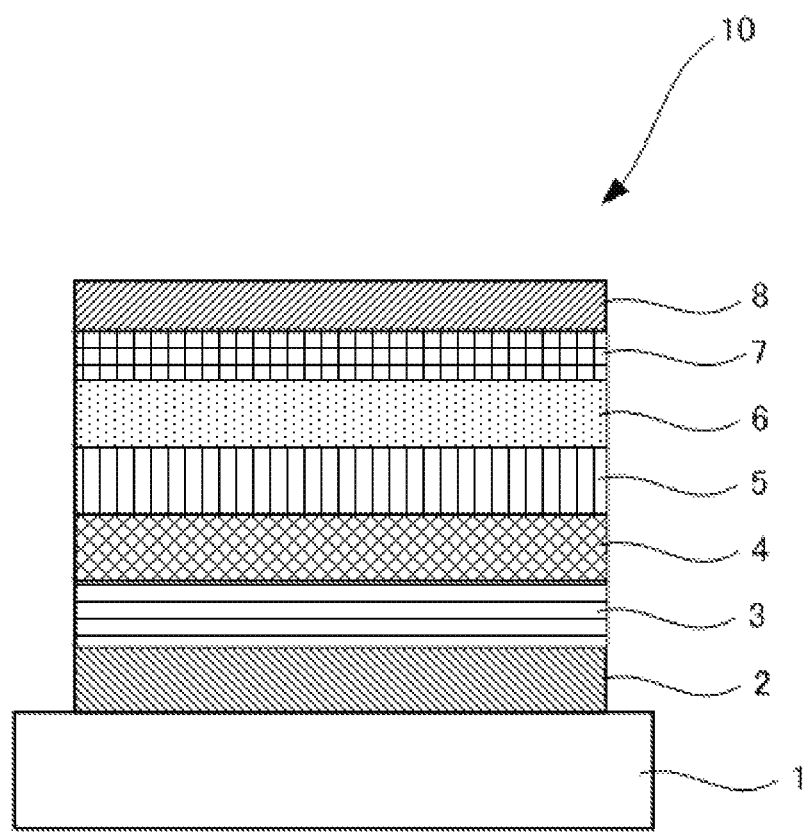

METHOD FOR PRODUCING ORGANIC ELECTROLUMINESCENCE ELEMENT

CROSS REFERENCE TO RELATED APPLICATIONS

This application is a National Stage of International Application No. PCT/JP2011/054740 filed Mar. 2, 2011, claiming priority based on Japanese Patent Application No. 2010-057556, filed Mar. 15, 2010, the contents of all of which are incorporated herein by reference in their entirety.

TECHNICAL FIELD

The present invention relates to a method for producing an organic electroluminescence device.

BACKGROUND ART

Organic electroluminescence devices have advantageous features such as self emission and high-speed response and are expected for the application to flat panel displays. In particular, since such organic electroluminescence devices were reported that have a dual-layer structure (lamination type) in which a hole-transporting organic thin film (hole transport layer) is laminated on an electron-transporting organic thin film (electron transport layer), organic electroluminescence devices have been attracting attention as a large-area light-emitting device that emits light at a low voltage of 10 V or lower. The organic electroluminescence devices of lamination type have a basic structure of anode/hole transport layer/emission layer/electron transport layer/cathode.

In order to improve the surface uniformity of such organic electroluminescence devices the following production methods have been proposed for example: (i) a production method where a mixture of polyethylenedioxythiophene (PEDOT)/polystyrene sulfonic acid (PSS) is leveled under high-temperature/high-humidity environments to form a hole transport layer (see, for example, PTL 1); (ii) a production method where heat treatment in a mode of being heated from the rear surface is performed at a temperature which falls within the range of −30° C. to +30° C. of the glass transition temperature of a light-emitting layer and which does not exceed the decomposition temperatures of organic compounds forming the light-emitting layer, a dicarbazole derivative (CBP) is used as a host material, and toluene is used as a solvent (see, for example, PTL 2); and (iii) a production method where an organic light-emitting medium layer is heated upon drying to a temperature equal to or higher than the boiling point of an organic solvent contained in a functional ink; i.e., around the glass transition temperature (Tg) (see, for example, PTL 3).

However, the organic electroluminescence devices produced by these production methods have a problem in that the surface uniformity of the light-emitting layer is not sufficient.

Therefore, at present, keen demand has arisen for development of a production method for an organic electroluminescence device the light-emitting layer of which has sufficient surface uniformity.

CITATION LIST

Patent Literature

PTL 1: U.S. Patent Application Publication No. 2005/0276910

PTL 2: Japanese Patent Application Laid-Open (JP-A) No. 2009-163889

PTL 3: JP-A No. 2009-129567

SUMMARY OF INVENTION

Technical Problem

The present invention aims to provide a method for producing an organic electroluminescence device, the method being capable of improving the surface uniformity of a light-emitting layer.

Solution to Problem

Means for solving the above existing problems are as follows.

<1> A method for producing an organic electroluminescence device which contains an anode, a cathode and an organic layer between the anode and the cathode where the organic layer contains a light-emitting layer and an adjacent layer adjacent to the light-emitting layer, the method including:

applying to the adjacent layer a coating liquid prepared by dissolving or dispersing a light-emitting material and a host material in a solvent, and heating the coating liquid applied to the adjacent layer at a temperature higher than a melting temperature of the host material and higher than a boiling point of the solvent, to thereby form the light-emitting layer, wherein a difference as an absolute value between contact angle A (°) of the light-emitting layer with respect to pure water and contact angle B (°) of the adjacent layer with respect to pure water is 13 (°) or smaller.

<2> The method for producing an organic electroluminescence device according to <1>, wherein the light-emitting material has a molecular weight of 1,500 or lower and the host material has a molecular weight of 1,500 or lower.

<3> The method for producing an organic electroluminescence device according to <1> or <2>, wherein the host material is a compound represented by the following General Formula (1) or (2):

General Formula (1)

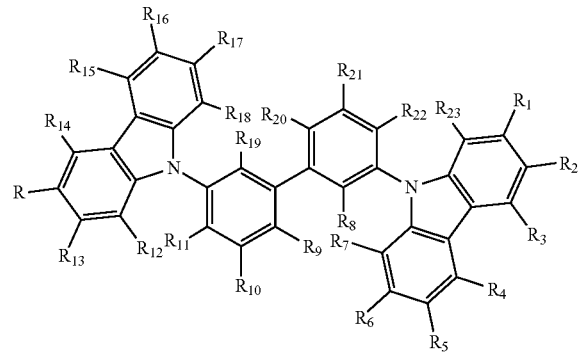

where R represents a t-butyl group, a t-amyl group, a trimethylsilyl group, a triphenylsilyl group or a phenyl group, and $R_1$ to $R_{23}$ each represent a hydrogen atom, a C1-C5 alkyl group, a cyano group, a fluorine atom, a trifluoro group, a trimethylsilyl group, a triphenylsilyl group or a phenyl group, General Formula (2)

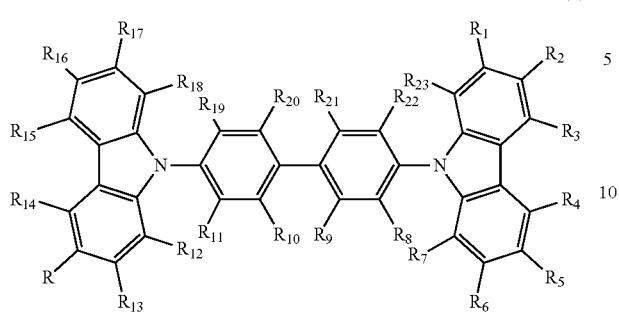

where R represents a t-butyl group, a t-amyl group, a trimethylsilyl group, a triphenylsilyl group or a phenyl group, and $R_1$ to $R_{23}$ each represent a hydrogen atom, a C1-C5 alkyl group, a cyano group, a fluorine atom, a trifluoro group, a trimethylsilyl group, a triphenylsilyl group or a phenyl group.

<4> The method for producing an organic electroluminescence device according to <1> or <2>, wherein the host material is a compound expressed by any one of the following Structural Formulas (1) to (4):

Structural Formula (1)

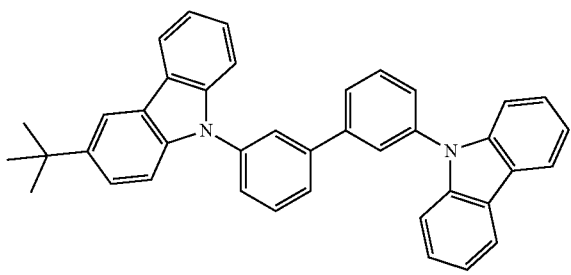

Structural Formula (2)

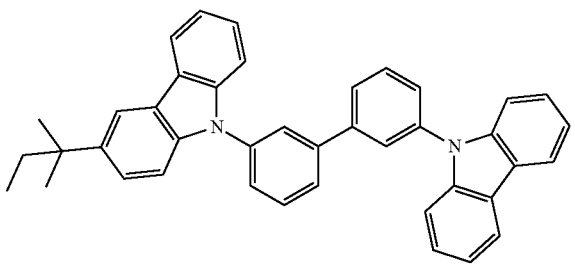

Structural Formula (3)

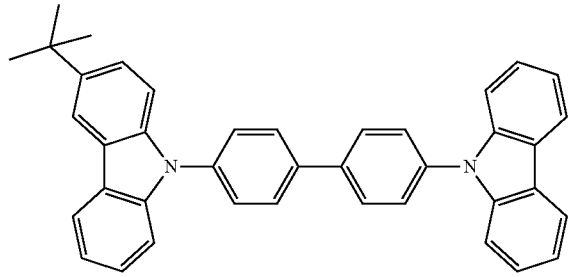

Structural Formula (4)

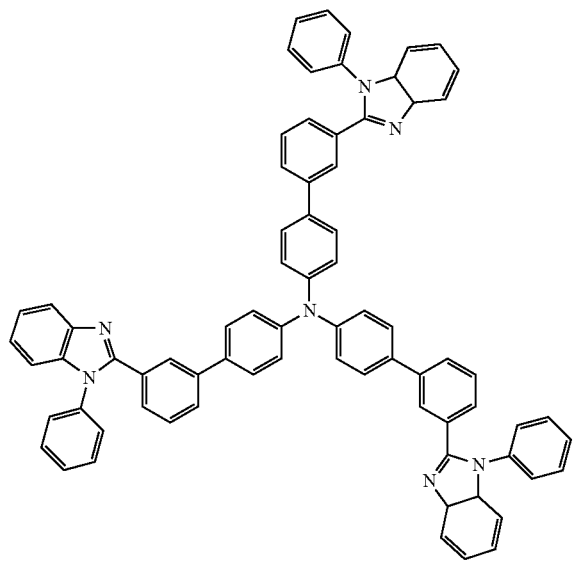

<5> The method for producing an organic electroluminescence device according to any one of <1> to <4>, wherein the solvent contains at least one selected from the group consisting of aromatic hydrocarbons and ketones each having a boiling point of 100° C. or higher.

<6> The method for producing an organic electroluminescence device according to any one of <1> to <5>, wherein the temperature of the heating is higher than the melting temperature of the host material by 20° C. or higher.

<7> The method for producing an organic electroluminescence device according to any one of <1> to <6>, wherein the light-emitting layer has an Ra value of 5 nm or more before the host material melts and the light-emitting layer has an Ra value of 1 nm or less after the host material melts.

Advantageous Effects of Invention

The present invention can provide a method for producing an organic electroluminescence device, the method being capable of improving the surface uniformity of a light-emitting layer. The method can solve the above existing problems and achieve the above objects.

BRIEF DESCRIPTION OF DRAWINGS

FIG. 1 is a schematic view of one exemplary layer structure of an organic electroluminescence device of the present invention.

DESCRIPTION OF EMBODIMENTS (Method for Producing Organic Electroluminescence Device)

A method of the present invention for producing an organic electroluminescence device includes at least a step of forming a light-emitting layer; and, if necessary, further includes appropriately selected other steps.

<Step of Forming a Light-Emitting Layer>

The step of forming a light-emitting layer is a step of applying, to an adjacent layer adjacent to a light-emitting layer, a coating liquid prepared by dissolving or dispersing a light-emitting material and a host material in a solvent, and heating the coating liquid applied to the adjacent layer to thereby form a light-emitting layer.

<<Light-Emitting Material>>

The light-emitting material is not particularly limited and may be appropriately selected depending on the intended purpose, but is preferably a compound having a molecular weight of 1,500 or lower.

When the light-emitting material is a mixture containing a plurality of compounds, the molecular weight of the light-emitting material means the molecular weight of a compound having the highest molecular weight.

In general, examples of the light-emitting material include complexes containing a transition metal atom or a lanthanoid atom. Preferred examples of the transition metal atom include ruthenium, rhodium, palladium, tungsten, rhenium, osmium, iridium and platinum, with rhenium, iridium and platinum being more preferred, with iridium and platinum being still more preferred.

Examples of the lanthanoid atom include lanthanum, cerium, praseodymium, neodymium, samarium, europium, gadolinium, terbium, dysprosium, holmium, erbium, thulium, ytterbium and lutetium, with neodymium, europium and gadolinium being preferred.

Examples of the ligand in the complexes include those described in, for example, "Comprehensive Coordination Chemistry" authored by G. Wilkinson et al., published by Pergamon Press Company in 1987; "Photochemistry and Photophysics of Coordination Compounds" authored by H. Yersin, published by Springer-Verlag Company in 1987; and "YUHKI KINZOKU KAGAKU—KISO TO OUYOU—(Metalorganic Chemistry—Fundamental and Application—)" authored by Akio Yamamoto, published by Shokabo Publishing Co., Ltd. in 1982.

Preferred specific examples of the ligand include halogen ligands, preferably, chlorine ligand; aromatic carbon ring ligands such as cyclopentadienyl anion, benzene anion and naphthyl anion; nitrogen-containing hetero cyclic ligands such as phenyl pyridine, benzoquinoline, quinolinol, bipyridyl and phenanthrorine); diketone ligands such as acetyl acetone; carboxylic acid ligands such as acetic acid ligand); alcoholate ligands such as phenolate ligand; carbon monoxide ligand; isonitrile ligand; and cyano ligand, with nitrogen-containing hetero cyclic ligands being more preferred.

The above-described complexes may be a complex containing one transition metal atom in the compound, or a so-called polynuclear complex containing two or more transition metal atoms. In the latter case, the complexes may contain different metal atoms at the same time.

Specific examples of the light-emitting material containing platinum include the following light-emitting material, but employable light-emitting materials are not construed as being limited thereto.

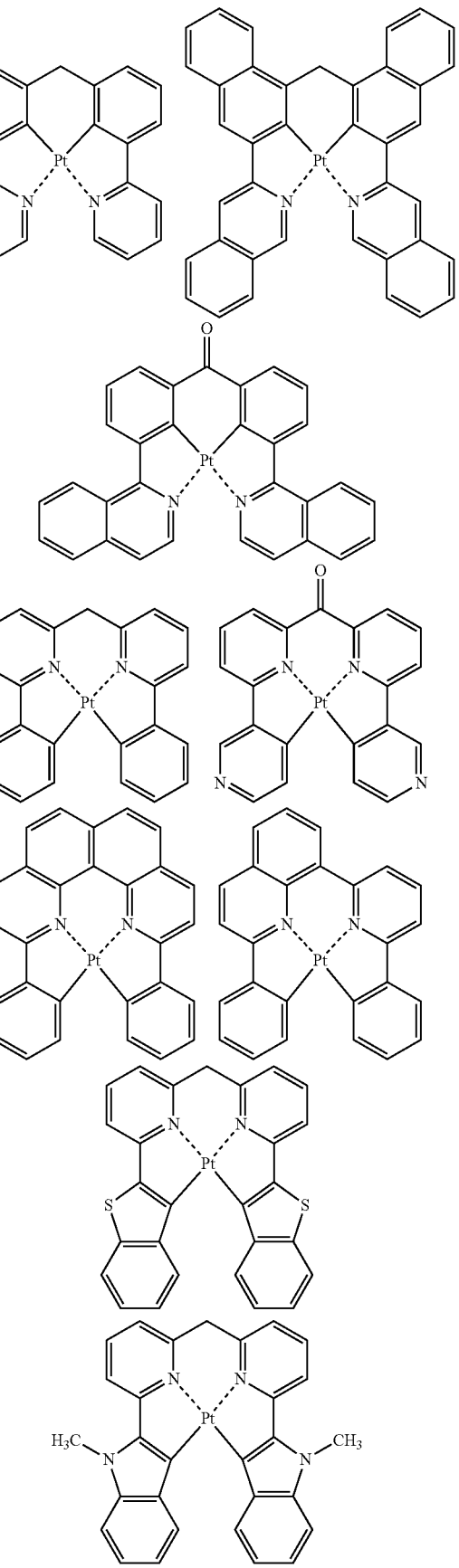

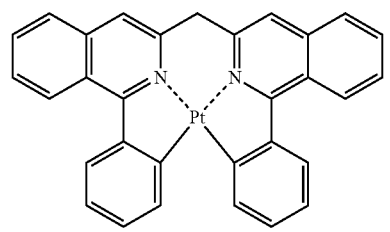
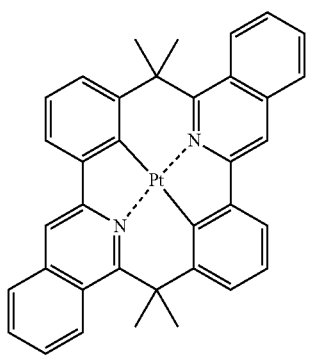
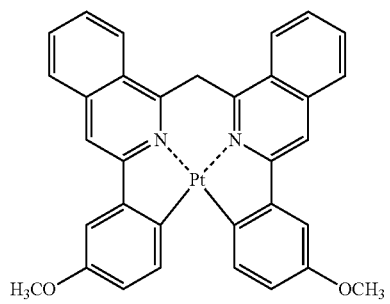
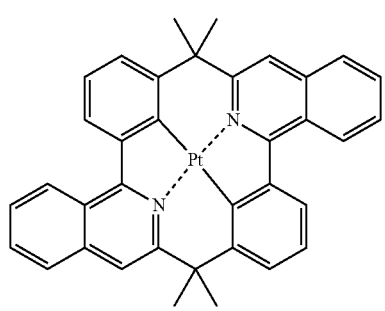
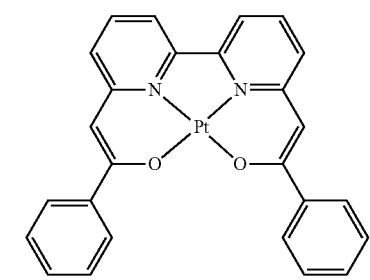
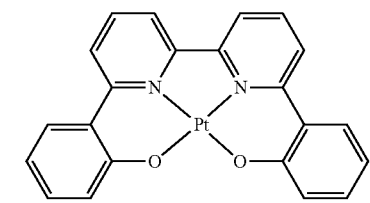
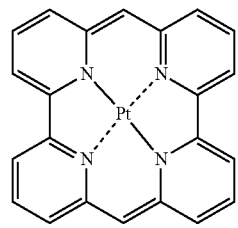
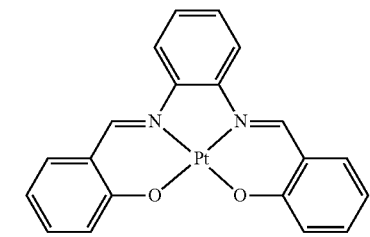
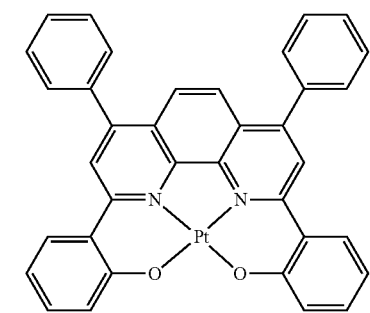
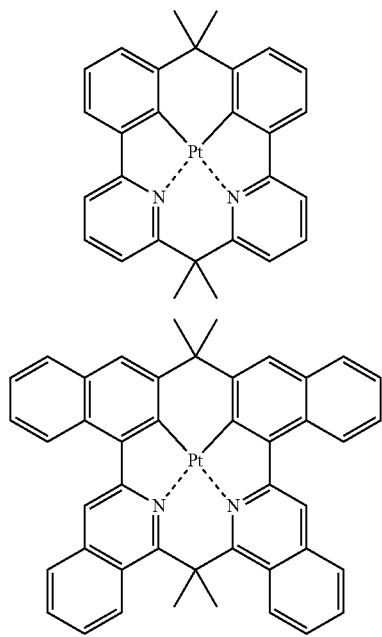

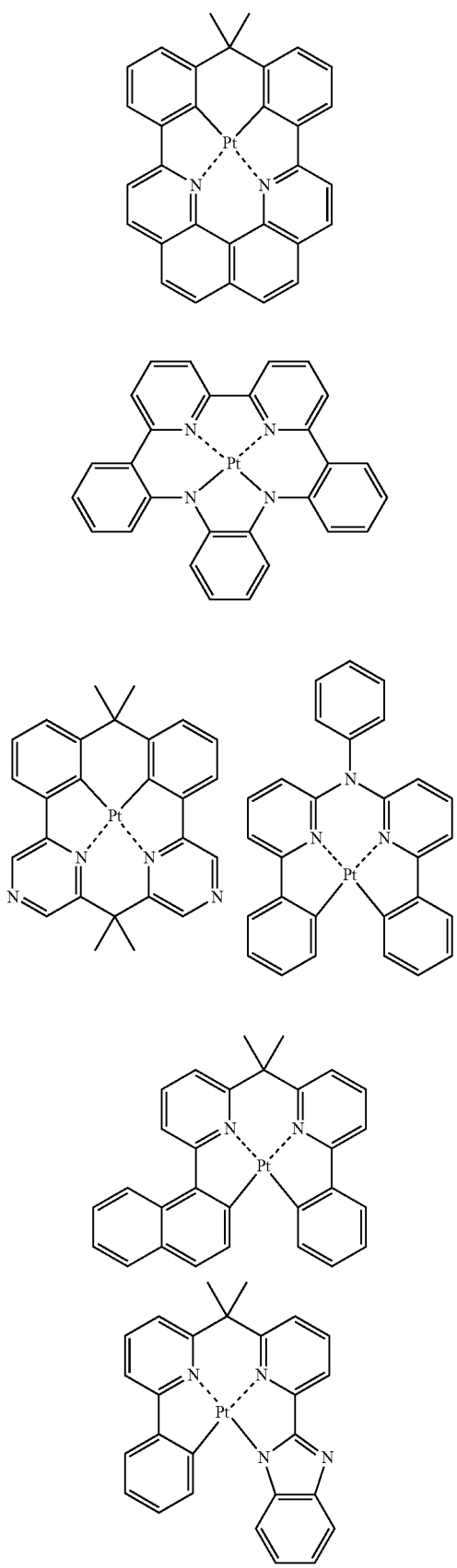
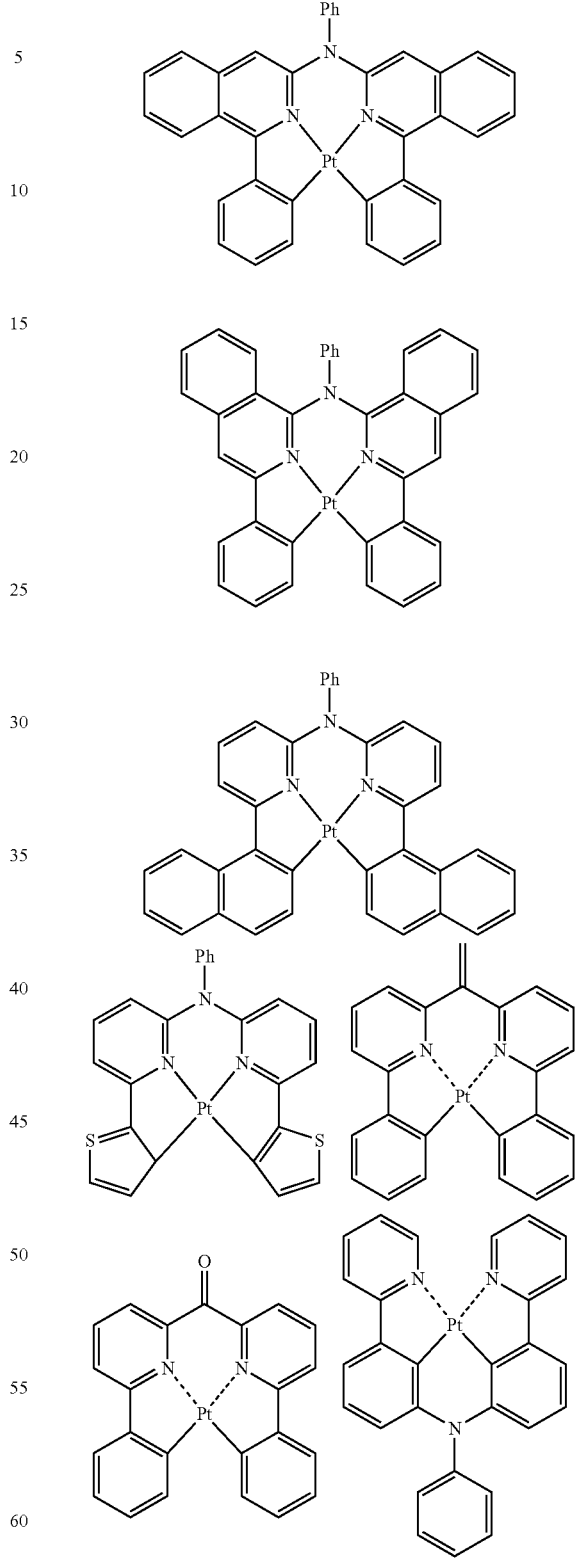
The light-emitting material containing iridium is not particularly limited and may be appropriately selected depending on the intended purpose, but is preferably the following compounds.

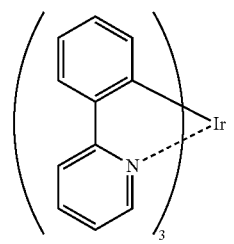
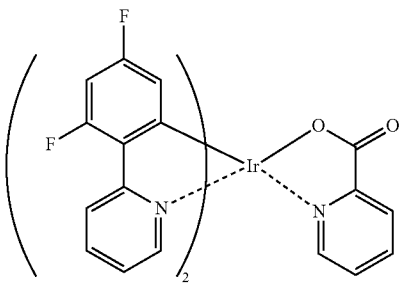
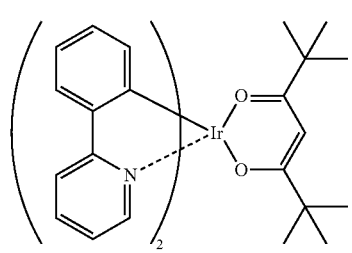
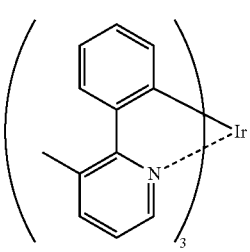
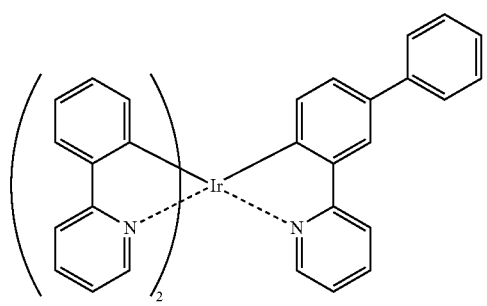
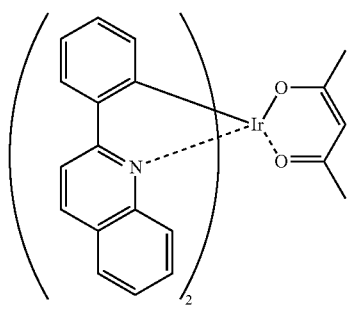
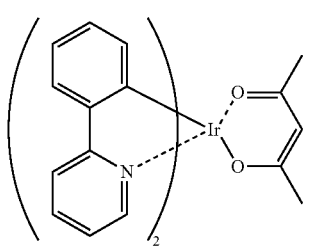
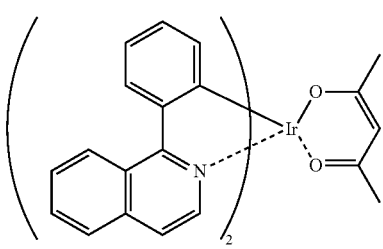
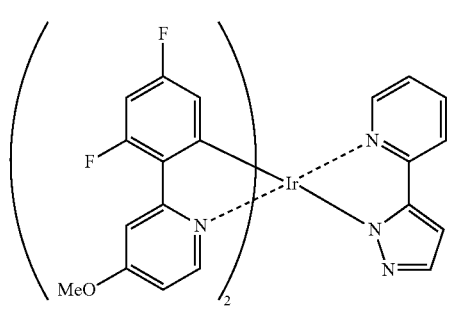
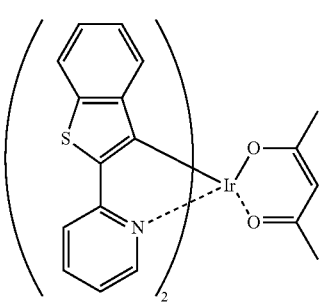

-continued

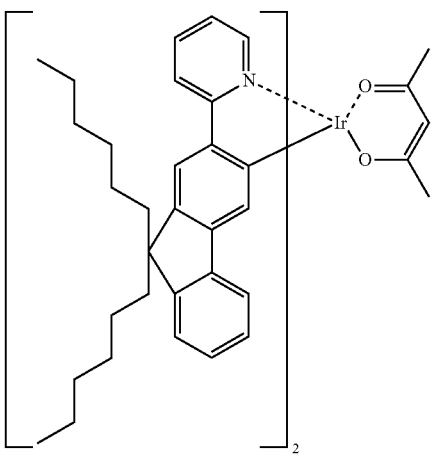

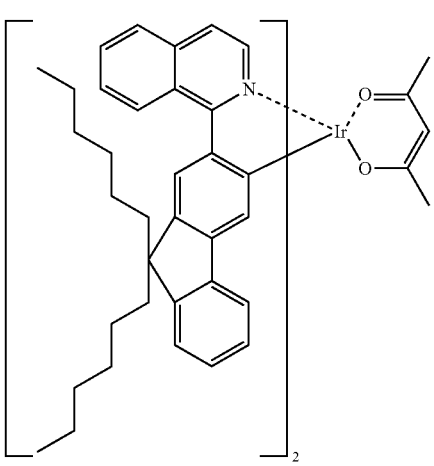

Host Material

The host material is not particularly limited and may be appropriately selected depending on the intended purpose, but is preferably a compound having a molecular weight of 1,500 or lower.

When the host material is a mixture containing a plurality of compounds, the molecular weight of the host material means the molecular weight of a compound having the highest molecular weight.

The host material is not particularly limited and may be appropriately selected depending on the intended purpose. Examples thereof include compounds represented by the following General Formulas (1) and (2). Specific examples thereof include compounds expressed by the following Structural Formulas (1) to (17).

General Formula (1)

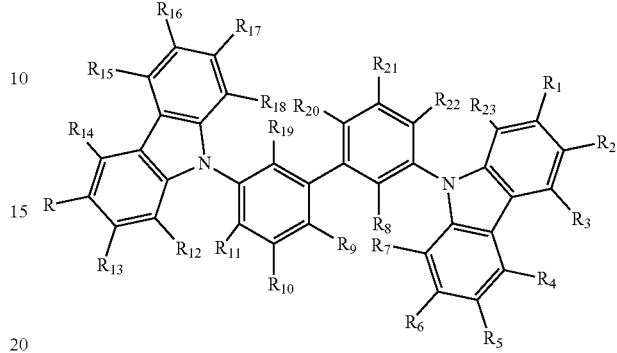

In General Formula (1), R represents a t-butyl group, a t-amyl group, a trimethylsilyl group, a triphenylsilyl group or a phenyl group, and $R_1$ to $R_{23}$ each represent a hydrogen atom, a C1-C5 alkyl group, a cyano group, a fluorine atom, a trifluoro group, a trimethylsilyl group, a triphenylsilyl group or a phenyl group.

General Formula (2)

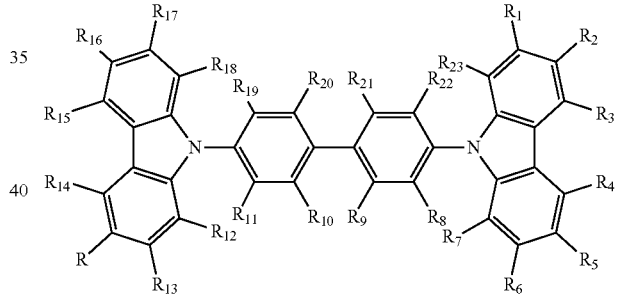

In General Formula (2), R represents a t-butyl group, a t-amyl group, a trimethylsilyl group, a triphenylsilyl group or a phenyl group, and $R_1$ to $R_{23}$ each represent a hydrogen atom, a C1-C5 alkyl group, a cyano group, a fluorine atom, a trifluoro group, a trimethylsilyl group, a triphenylsilyl group or a phenyl group.

Structural Formula (1)

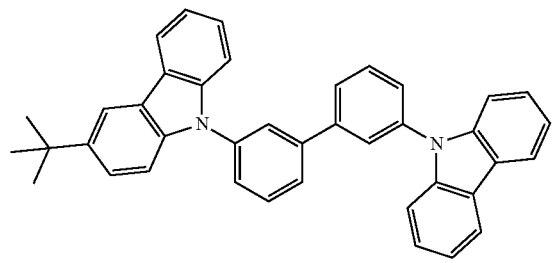

Structural Formula (2)

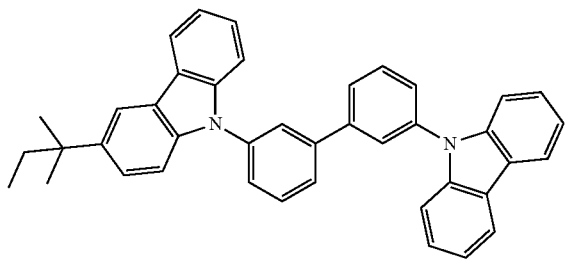

-continued
Structural Formula (3)
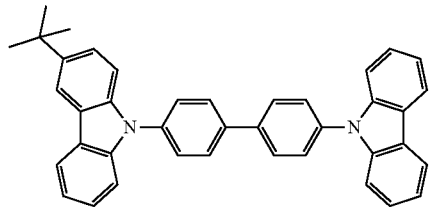
Structural Formula (4)
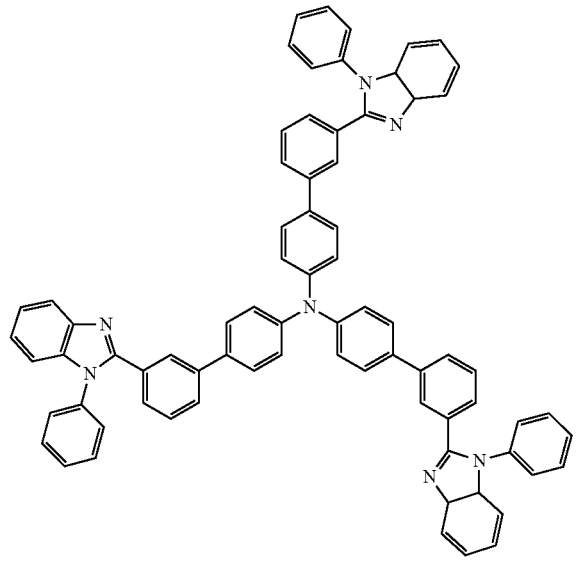
Structural Formula (5)
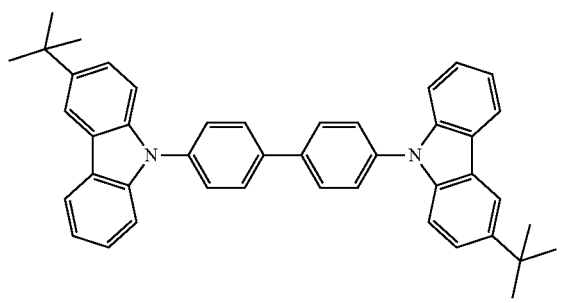
Structural Formula (6)
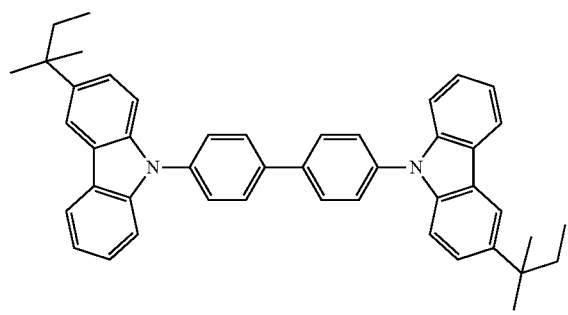
Structural Formula (7)
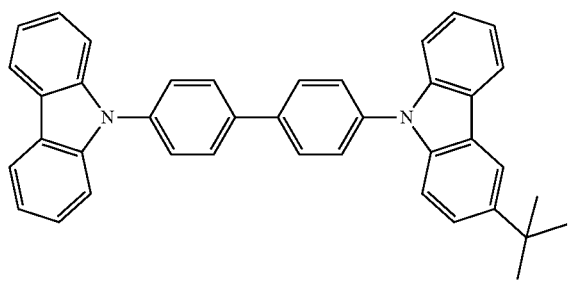
Structural Formula (8)
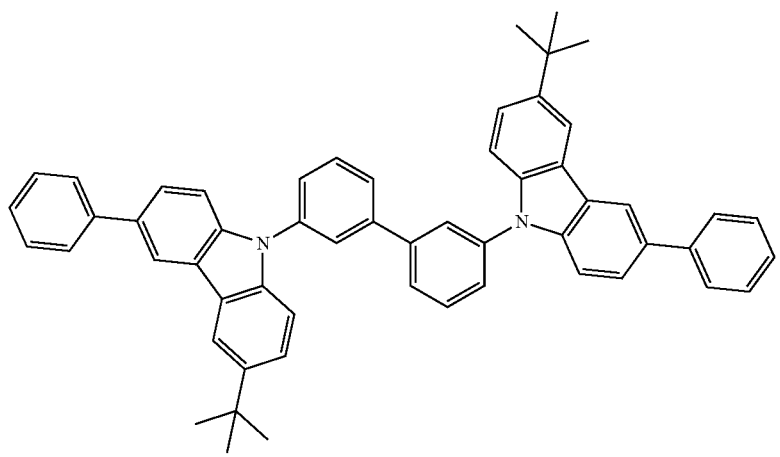

Structural Formula (9)
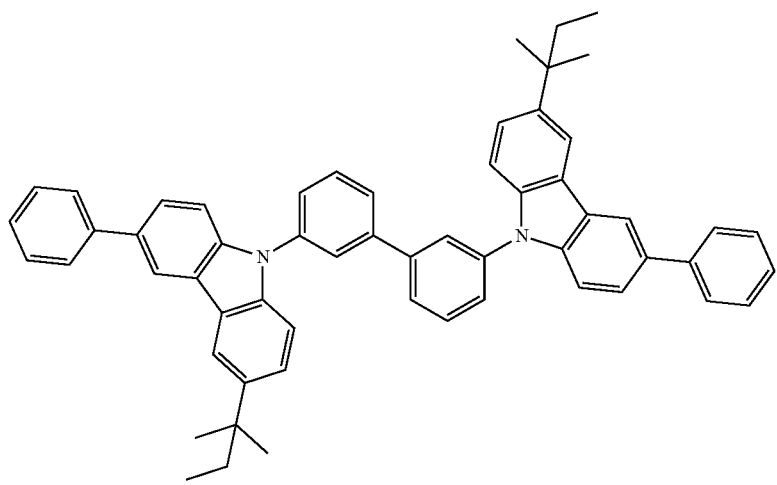
Structural Formula (10)
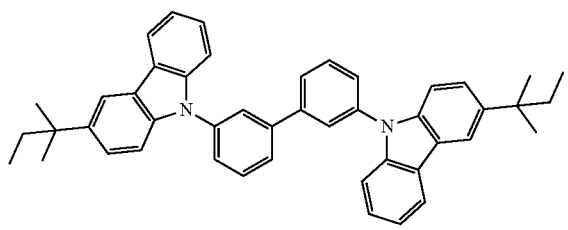
Structural Formula (11)
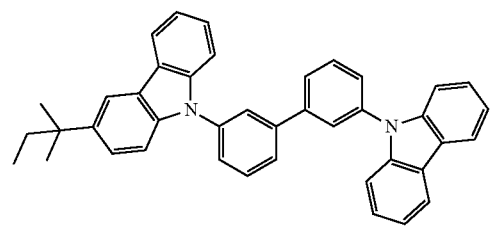
Structural Formula (12)
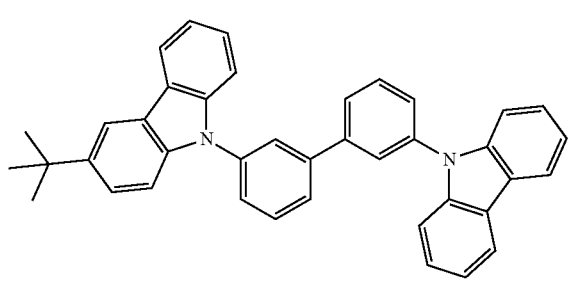
Structural Formula (13)
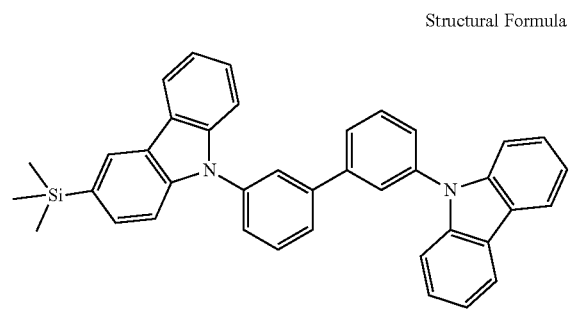
Structural Formula (14)
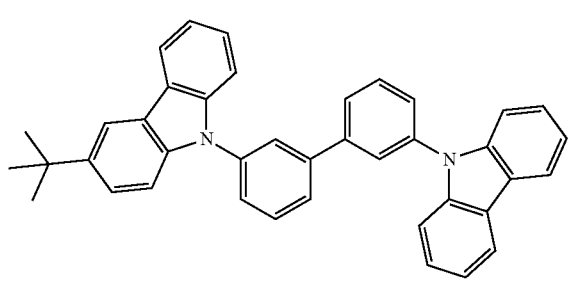
Structural Formula (15)
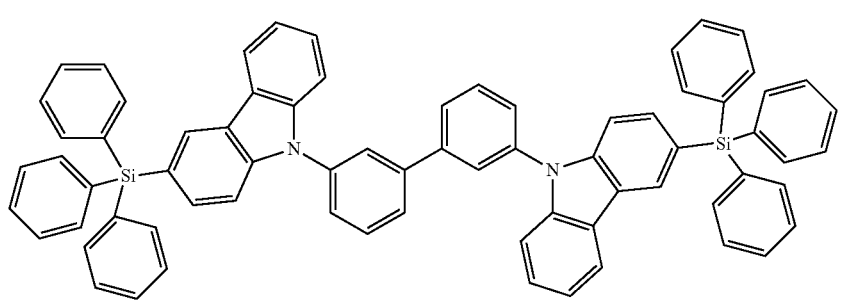

Structural Formula (16)

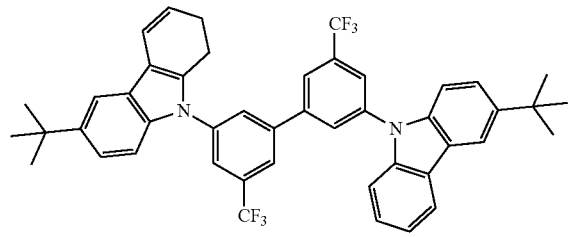

Structural Formula (17)

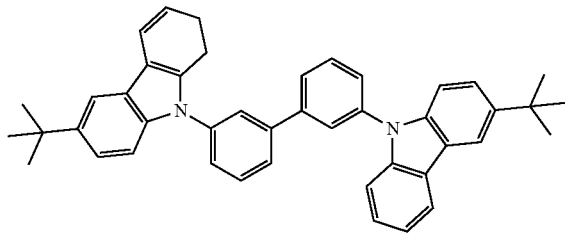

The melting temperature of the host material means a temperature at which the host material changes from a solid phase to a liquid phase. The melting temperature thereof can be measured in the following manner.
<Measuring Method for Melting Temperature>
The melting temperature can be measured through differential scanning calorimetry or with a melting point measuring apparatus. In the present invention, the temperature at which powder melts can be observed under an optical microscope by heating the powder on a hot stage.

When the host material is a mixture containing a plurality of compounds, the melting temperature of the host material means the melting temperature of a compound having the highest melting temperature.
Solvent The solvent is not particularly limited and may be appropriately selected depending on the intended purpose. Examples thereof include: aromatic hydrocarbons such as trimethylbenzene, cumene, xylene and toluene; and ketones such as cyclohexane, diisobutyl ketone and methyl isobutyl ketone. These may be used alone or in combination.

Among them, xylene, toluene and cumene are preferred from the viewpoint of storage stability of the coating liquid prepared.

When the solvent is a solvent mixture containing a plurality of solvents, the boiling point of the solvent means the boiling point of a solvent having the highest boiling point.

The amount of solid matters (host material and phosphorescent light-emitting material) contained in the coating liquid is not particularly limited and may be appropriately selected depending on the intended purpose, but is preferably 0.001% by mass to 20% by mass, more preferably 0.01% by mass to 15% by mass, particularly preferably 0.1% by mass to 10% by mass.

When the amount of the above solid matters is less than 0.001% by mass, the takt time may become long; i.e., the time required for application may become long. When it is more than 20% by mass, there may be clogging in an inkjet nozzle or a spray. Meanwhile, when the amount of the above solid matters falls within the above particularly preferred range, the takt time becomes short and maintenance of the apparatus is not necessary, which is advantageous.

The ratio of the light-emitting material:the host material is not particularly limited and may be appropriately selected depending on the intended purpose, but is preferably 1:99 to 30:70, more preferably 2:98 to 20:80, particularly preferably 4:96 to 15:75.

When the ratio of the light-emitting material:the host material is (less than 1):(more than 99), EL light emission cannot be obtained in some cases. When it is (more than 30):(less than 70), EL light emission efficiency may decrease due to concentration quenching. Meanwhile, when the ratio of the light-emitting material:the host material falls within the above particularly preferred range, high light emission efficiency can advantageously be obtained.
<<Application>>
The method for the application is not particularly limited and may be appropriately selected depending on the intended purpose, so long as it can apply the coating liquid prepared by dissolving or dispersing the light-emitting material and the host material in the solvent. Examples thereof include spin coating, inkjet coating and mist spraying such as spray coating.
<<Heating>>
The heating temperature in the heating is not particularly limited and may be appropriately selected depending on the intended purpose, so long as it is a temperature higher than the melting temperature of the host material and higher than the boiling point of the solvent. The heating temperature is preferably higher than the melting temperature of the host material by 20° C. or higher.

When the heating temperature is lower than the melting temperature of the host material, leveling cannot be performed in some cases. When the heating temperature is lower than the boiling point of the solvent, the solvent remains in the light-emitting layer, potentially degrading the EL light emission efficiency and durability of the organic electroluminescence device. Meanwhile, the heating temperature that falls within the above preferred range is advantageous in that the light-emitting layer can be leveled, no solvent remains, uniform light emission can be obtained, and the light emission efficiency of the organic electroluminescence device can be improved.

When the host material is a mixture containing a plurality of compounds, the heating temperature has to be higher than the melting temperatures of all the compounds in the mixture. In other words, the heating temperature has to be higher than the highest melting temperature among the melting temperatures of the compounds in the mixture.

When the solvent is a solvent mixture containing a plurality of solvents, the heating temperature has to be higher than the boiling points of all the solvents in the solvent mixture. In other words, the heating temperature has to be higher than the highest boiling point among the boiling points of the solvents in the solvent mixture.

The heating time in the heating is not particularly limited and may be appropriately selected depending on the intended purpose, but is preferably 1 min to 5 hours, more preferably 5 min to 1 hour, particularly preferably 5 min to 30 min.

When the heating time is shorter than 1 min, the solvent remains in the light-emitting layer, potentially degrading the EL light emission efficiency and durability of the organic electroluminescence device. When it is longer than 5 hours, there may be decomposition by oxidation and delamination of films. Meanwhile, the heating time that falls within the above particularly preferred range is advantageous in that no solvent remains, uniform light emission can be obtained, and the light emission efficiency of the organic electroluminescence device can be improved.

The heating may be performed any times which are appropriately selected depending on the intended purpose. The heating may be performed once or twice or more. When the heating is performed twice or more, the heating temperatures or the heating times may be identical or different in the heating performed twice or more.

<<Contact Angles of Light-Emitting Layer and Adjacent Layer>>

The contact angle means a contact angle with respect to pure water and measured in the following manner.

Measurement Method for Contact Angle

The contact angle can be measured with a contact angle meter (e.g., full-automatic contact angle meter DM-301, product of Kyowa Interface Science Co., Ltd.).

The difference as an absolute value between contact angle A of the light-emitting layer with respect to pure water and contact angle B of the adjacent layer with respect to pure water is not particularly limited, so long as it is 13° or smaller, and may be appropriately selected depending on the intended purpose. It is preferably 13° or smaller, more preferably 10° or smaller, particularly preferably 5° or smaller.

When the above difference as an absolute value is greater than 13°, the light-emitting layer may be peeled off at the interface with the underlying layer when subjected to melting. The above difference that falls within the above particularly preferred range is advantageous in terms of adhesiveness between the layers.

The adjacent layer is not particularly limited and may be appropriately selected depending on the intended purpose, so long as it is formed before the formation of the light-emitting layer and is adjacent to the light-emitting layer. Examples thereof include a hole injection layer and a hole transport layer.

<<Ra Value>>

The Ra value (nm) means a value obtained through a process including: folding a roughness curve along the center line; measuring the area formed by the roughness curve and the center line; and dividing the area by the measurement length (i.e., the length of the center line). Specifically, the Ra value is measured in the following manner.

Measurement Method for Ra

An AFM, a confocal microscope, a light interference optical microscope, or other instruments can be used to measure the surface roughness (Ra) of any region. The size of the region measured is preferably 10 μm×10 μm to 5 mm×5 mm.

The light-emitting layer formed by the spray method generally has an Ra value of 5 nm or more before the host material in the light-emitting layer melts.

The Ra value of the light-emitting layer after the host material in the light-emitting layer has melted is not particularly limited and may be appropriately selected depending on the intended purpose, but is preferably 1 nm or less, more preferably 0.5 nm or less, particularly preferably 0.2 nm or less.

When the Ra value is more than 1 nm, the adjacent layer (electron transport layer) fluctuates in thickness and the light emission intensity may be varied from place to place on the light-emission surface. The Ra value of the light-emitting layer that falls within the above particularly preferred range is advantageous since it is possible to obtain uniform light emission on the light-emission surface.

<Hole Injection Layer-Forming Step>

The hole injection layer-forming step is a step of forming the hole injection layer.

The method for forming the hole injection layer is not particularly limited and may be appropriately selected depending on the intended purpose. Examples thereof include: dry film forming methods such as a vapor deposition method and a sputtering method; wet coating methods; transfer methods; printing methods; and inkjet methods.

<Hole Transport Layer-Forming Step>

The hole transport layer-forming step is a step of forming the hole transport layer.

The method for forming the hole transport layer is not particularly limited and may be appropriately selected depending on the intended purpose. Examples thereof include: dry film forming methods such as a vapor deposition method and a sputtering method; wet coating methods; transfer methods; printing methods; and inkjet methods.

<Other Steps>

The other steps are not particularly limited and may be appropriately selected depending on the intended purpose. Examples thereof include an electron transport layer-forming step, an electron injection layer-forming step, a hole blocking layer-forming step and an electron blocking layer-forming step.

<Organic Electroluminescence Device>

The organic electroluminescence device includes a pair of electrodes (anode and cathode) and an organic layer between the electrodes; and, if necessary, may further include appropriately selected other layers.

The organic layer includes at least a light-emitting layer; and, if necessary, may further include a hole transport layer, an electron transport layer, a hole blocking layer, an electron blocking layer, a hole injection layer and an electron injection layer.

<<Light-Emitting Layer>>

The light-emitting layer contains the light-emitting material and the host material. The light-emitting layer is a layer having the functions of receiving holes from the anode, the hole injection layer, or the hole transport layer, and receiving electrons from the cathode, the electron injection layer, or the electron transport layer, and providing a field for recombination of the holes with the electrons for light emission, when an electric field is applied.

The thickness of the light-emitting layer is not particularly limited and may be appropriately selected depending on the intended purpose. The thickness thereof is preferably 2 nm to 500 nm. From the viewpoint of increasing the external quantum efficiency, the thickness thereof is more preferably 3 nm to 200 nm, particularly preferably 10 nm to 200 nm. The light-emitting layer may be a single layer or two or more layers. When it is two or more layers, the layers may emit lights of different colors.

<<Hole Injection Layer and Hole Transport Layer>>

The hole injection layer and hole transport layer are layers having the function of receiving holes from the anode or from the anode side and transporting the holes to the cathode side. Each of the hole injection layer and the hole transport layer may have a single-layered structure or a multi-layered structure made of a plurality of layers which are identical or different in composition.

Hole Injection Material and Hole Transport Material

Hole injection materials or hole transport materials used in the hole injection layer or the hole transport layer may be, for example, low-molecular-weight compounds and high-molecular-weight compounds.

The hole injection materials or the hole transport materials are not particularly limited and may be appropriately selected depending on the intended purpose. Examples thereof include pyrrole derivatives, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidine compounds, phthalocyanine compounds, porphyrin compounds, thiophene derivatives, organosilane derivatives and carbon. These may be use alone or in combination.

The hole injection layer or the hole transport layer may contain an electron-accepting dopant.

The electron-accepting dopant may be an inorganic or organic compound, so long as it has electron accepting property and the property of oxidizing an organic compound.

The inorganic compound is not particularly limited and may be appropriately selected depending on the intended purpose. Examples thereof include metal halides (e.g., ferric chloride, aluminum chloride, gallium chloride, indium chloride and antimony pentachloride) and metal oxides (e.g., vanadium pentaoxide and molybdenum trioxide).

The organic compound is not particularly limited and may be appropriately selected depending on the intended purpose. Examples thereof include compounds having a substituent such as a nitro group, a halogen, a cyano group and a trifluoromethyl group; quinone compounds; acid anhydride compounds; and fullerenes.

These electron-accepting dopants may be used alone or in combination.

The amount of the electron-accepting dopant used varies depending on the type of the material. The amount thereof is preferably 0.01% by mass to 50% by mass, more preferably 0.05% by mass to 20% by mass, particularly preferably 0.1% by mass to 10% by mass, relative to the hole transport material or the hole injection material.

The thickness of the hole injection layer or the hole transport layer is preferably 1 nm to 500 nm, more preferably 5 nm to 200 nm, particularly preferably 10 nm to 100 nm.

<<Electron Transport Layer and Electron Injection Layer>>

The electron injection layer or the electron transport layer is a layer having the function of receiving electrons from the cathode or from the cathode side and transporting the electrons to the anode side.

The electron injection layer or the electron transport layer preferably contains a reducing dopant.

The reducing dopant is not particularly limited and may be appropriately selected depending on the intended purpose. The reducing dopant is preferably at least one selected from alkali metals, alkaline-earth metals, rare-earth metals, alkali metal oxides, alkali metal halides, alkaline-earth metal oxides, alkaline-earth metal halides, rare-earth metal oxides, rare-earth metal halides, alkali metal organic complexes, alkaline-earth metal organic complexes and rare-earth metal organic complexes.

The amount of the reducing dopant used varies depending on the type of the material. The amount thereof is preferably 0.1% by mass to 99% by mass, more preferably 0.3% by mass to 80% by mass, particularly preferably 0.5% by mass to 50% by mass, relative to the electron transport material or the electron injection material.

The electron transport layer and the electron injection layer can be formed by a known method. Specifically, suitably employed methods include vapor deposition methods, wet film forming methods, molecular beam epitaxial (or MBE) methods, cluster ion beam methods, molecule deposition methods, LB methods, printing methods and transfer methods.

The thickness of the electron transport layer is not particularly limited and may be appropriately selected depending on the intended purpose. The thickness thereof is preferably 1 nm to 200 nm, more preferably 1 nm to 100 nm, particularly preferably 1 nm to 50 nm.

The thickness of the electron injection layer is not particularly limited and may be appropriately selected depending on the intended purpose. The thickness thereof is preferably 1 nm to 200 nm, more preferably 1 nm to 100 nm, particularly preferably 1 nm to 50 nm.

<<Hole Blocking Layer and Electron Blocking Layer>>

The hole blocking layer is a layer having the function of preventing the holes, which have been transported from the anode side to the emission layer, from passing toward the cathode side, and is generally provided as an organic compound layer adjacent to the light-emitting layer on the cathode side.

The electron blocking layer is a layer having the function of preventing the electrons, which have been transported from the cathode side to the light-emitting layer, from passing toward the anode side, and is generally provided as an organic compound layer adjacent to the light-emitting layer on the anode side.

Examples of the compound employable for the hole blocking layer include aluminium complexes (e.g., BAlq), triazole derivatives and phenanthroline derivatives (e.g., BCP).

Examples of the compound employable for the electron blocking layer include the above-described hole transport materials.

The electron blocking layer and the hole blocking layer are not particularly limited and can be formed by a known method. Specifically, suitably employed methods include: dry film forming methods such as vapor deposition methods or sputtering methods; wet coating methods; transfer methods; printing methods; and inkjet methods.

The thickness of the hole blocking layer or the electron blocking layer is preferably 1 nm to 200 nm, more preferably 1 nm to 50 nm, particularly preferably 3 nm to 10 nm. The hole blocking layer or the electron blocking layer may have a single-layered structure made of one or more of the above-mentioned materials, or a multi-layered structure made of a plurality of layers which are identical or different in composition.

<<Electrode>>

The organic electroluminescence device includes a pair of electrodes; i.e., an anode and a cathode. In terms of the function of the organic electroluminescence device, at least one of the anode and the cathode is preferably transparent. In general, the anode has at least the function of serving as an electrode which supplies holes to the organic compound layer, and the cathode has at least the function of serving as an electrode which supplies electrons to the organic compound layer.

The shape, structure, size, etc. of the electrodes are not particularly limited and may be appropriately selected from known electrode materials depending on the intended application/purpose of the organic electroluminescence device.

Examples of the material for the electrodes include metals, alloys, metal oxides, electroconductive compounds and mixtures thereof.

<<Anode>>

Examples of the material for the anode include electroconductive metal oxides such as tin oxides doped with, for example, antimony and fluorine (ATO and FTO), tin oxide, zinc oxide, indium oxide, indium tin oxide (ITO) and indium zinc oxide (IZO); metals such as gold, silver, chromium and nickel; mixtures or laminates of these metals and the above electroconductive metal oxides; inorganic electroconductive materials such as copper iodide and copper sulfide; organic electroconductive materials such as polyaniline, polythiophene and polypyrrole; and laminates of these materials and ITO. Among them, electroconductive metal oxides are preferred. In particular, ITO is preferred from the viewpoints of, for example, productivity, high conductivity and transparency.

Cathode

Examples of the material for the cathode include alkali metals (e.g., Li, Na, K and Cs), alkaline-earth metals (e.g., Mg and Ca), gold, silver, lead, aluminum, sodium-potassium alloys, lithium-aluminum alloys, magnesium-silver alloys and rare earth metals (e.g., indium and ytterbium). These may be used alone, but it is preferred that two or more of them are used in combination from the viewpoint of satisfying both stability and electron-injection property.

Among them, alkali metals or alkaline earth metals are preferred in terms of excellent electron-injection property, and materials containing aluminum as a major component are preferred in terms of excellent storage stability.

The term "material containing aluminum as a major component" refers to a material composed of aluminum alone; alloys containing aluminum and 0.01% by mass to 10% by mass of an alkali or alkaline earth metal; or mixtures thereof (e.g., lithium-aluminum alloys and magnesium-aluminum alloys).

The method for forming the electrodes is not particularly limited and may be a known method. Examples thereof include wet methods such as printing methods and coating methods; physical methods such as vacuum vapor deposition methods, sputtering methods and ion plating methods; and chemical methods such as CVD and plasma CVD methods. The electrodes can be formed on a substrate by a method appropriately selected from the above methods in consideration of their suitability to the material for the electrodes. For example, when ITO is used as the material for the anode, the anode may be formed in accordance with a DC or high-frequency sputtering method, a vacuum vapor deposition method, or an ion plating method. For example, when a metal (or metals) is (are) selected as the material (or materials) for the cathode, one or more of them may be applied simultaneously or sequentially by, for example, a sputtering method.

Patterning for forming the electrodes may be performed by a chemical etching method such as photolithography; a physical etching method such as etching by laser; a method of vacuum deposition or sputtering using a mask; a lift-off method; or a printing method.

<<Substrate>>

The organic electroluminescence device is preferably formed on a substrate. It may be formed so that a substrate comes into direct contact with the electrodes, or may be formed on a substrate by the mediation of an intermediate layer.

The material for the substrate is not particularly limited and may be appropriately selected depending on the intended purpose. Examples thereof include inorganic materials such as yttria-stabilized zirconia (YSZ) and glass (alkali-free glass and soda-lime glass); and organic materials such as polyesters (e.g., polyethylene terephthalate, polybutylene phthalate and polyethylene naphthalate), polystyrene, polycarbonate, polyether sulfone, polyarylate, polyimide, polycycloolefin, norbornene resins and poly(chlorotrifluoroethylene).

The shape, structure, size, etc. of the substrate are not particularly limited and may be appropriately selected depending on, for example, the intended application/purpose of the organic electroluminescence device. In general, the substrate is preferably a sheet. The substrate may have a single- or multi-layered structure, and may be a single member or a combination of two or more members. The substrate may be opaque, colorless transparent, or colored transparent.

The substrate may be provided with a moisture permeation-preventing layer (gas barrier layer) on the front or back surface thereof.

The moisture permeation-preventing layer (gas barrier layer) is preferably made from an inorganic compound such as silicon nitride and silicon oxide.

The moisture permeation-preventing layer (gas barrier layer) may be formed through, for example, high-frequency sputtering.

<Protective Layer>

The organic electroluminescence may be entirely protected with a protective layer.

The material contained in the protective layer may be any materials, so long as they have the function of preventing permeation of water, oxygen, etc., which promote degradation of the device. Examples thereof include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$ and $TiO_2$; metal nitrides such as $SiN_x$ and $SiN_xO_y$; metal fluorides such as $MgF_2$, LiF, $AlF_3$ and $CaF_2$; polyethylenes, polypropylenes, polymethyl methacrylates, polyimides, polyureas, polytetrafluoroethylenes, polychlorotrifluoroethylens, polydichlorodifluoroethylenes, copolymers of chlorotrifluoroethylens and dichlorodifluoroethylenes, copolymers produced through compolymerization of a monomer mixture containing tetrafluoroethylene and at least one comonomer, fluorine-containing copolymers containing a ring structure in the copolymerization main chain, water-absorbing materials each having a water absorption rate of 1% or more, and moisture permeation preventive substances each having a water absorption rate of 0.1% or less.

The method for forming the protective layer is not particularly limited and may be appropriately selected depending on the intended purpose. Examples thereof include vacuum vapor deposition methods, sputtering methods, reactive sputtering methods, MBE (molecular beam epitaxial) methods, cluster ion beam methods, ion plating methods, plasma polymerization methods (high-frequency excitation ion plating methods), plasma CVD methods, laser CVD methods, thermal CVD methods, gas source CVD methods, coating methods, printing methods and transfer methods.

<<Seal Container>>

The organic electroluminescence device may be entirely sealed with a seal container. Moreover, a moisture absorber or an inert liquid may be incorporated into the space between the seal container and the organic electroluminescence device.

The moisture absorber is not particularly limited and may be appropriately selected depending on the intended purpose. Examples thereof include barium oxide, sodium oxide, potassium oxide, calcium oxide, sodium sulfate, calcium sulfate, magnesium sulfate, phosphorus pentaoxide, calcium chloride, magnesium chloride, copper chloride, cesium fluoride, niobium fluoride, calcium bromide, vanadium bromide, molecular sieve, zeolite and magnesium oxide.

Also, the inert liquid is not particularly limited and may be appropriately selected depending on the intended purpose. Examples thereof include paraffins; liquid paraffins; fluorine-containing solvents such as perfluoroalkanes, perfluoroamines and perfluoroethers; chlorine-containing solvents; and silicone oils.

<<Resin Seal Layer>>

The organic electroluminescence device is preferably sealed with a resin seal layer to prevent degradation of its performance due to oxygen or water contained in the air.

The resin material for the resin seal layer is not particularly limited and may be appropriately selected depending on the intended purpose. Examples thereof include acrylic resins, epoxy resins, fluorine-containing resins, silicone resins, rubber resins and ester resins. Among them, epoxy resins are preferred from the viewpoint of preventing water permeation. Among the epoxy resins, thermosetting epoxy resins and photo-curable epoxy resins are preferred.

The forming method for the resin seal layer is not particularly limited and may be appropriately selected depending on the intended purpose. Examples thereof include a method by coating a resin solution, a method by press-bonding or hot press-bonding a resin sheet, and a method by polymerizing under dry conditions (e.g., vapor deposition and sputtering).

<Sealing Adhesive>

The sealing adhesive used in the present invention has the function of preventing permeation of moisture or oxygen from the edges of the organic electroluminescence device.

The material for the sealing adhesive may be those used in the resin seal layer. Among them, epoxy adhesives are preferred from the viewpoint of preventing water permeation. Among the epoxy adhesives, photo-curable adhesives and thermosetting adhesives are preferred.

Also, a filler is preferably added to the sealing adhesive. Preferred examples of the filler include inorganic materials such as $SiO_2$, SiO (silicon oxide), SiON (silicon oxynitride) and SiN (silicon nitride). The addition of the filler increases the viscosity of the sealing adhesive to improve production suitability and humidity resistance.

The sealing adhesive may also contain a desiccant. Examples of the desiccant include barium oxide, calcium oxide and strontium oxide. The amount of the desiccant added to the sealing adhesive is preferably 0.01% by mass to 20% by mass, more preferably 0.05% by mass to 15% by mass. When the amount is less than 0.01% by mass, the desiccant exhibits reduced effects. Whereas when the amount is more than 20% by mass, it may be difficult to homogeneously disperse the desiccant in the sealing adhesive.

In the present invention, the sealing adhesive containing the desiccant is applied in a predetermined amount using, for example, a dispenser. Thereafter, a second substrate is overlaid, followed by curing for sealing.

FIG. 1 is a schematic view of one exemplary layer structure of the organic electroluminescence device. An organic electroluminescence device 10 has a layer structure in which a glass substrate 1 and an anode 2 (e.g., an ITO electrode), a hole injection layer 3, a hole transport layer 4, a light-emitting layer 5, an electron transport layer 6, an electron injection layer 7 (e.g., a lithium fluoride-containing layer) and a cathode 8 (e.g., an Al—Li electrode) disposed on the glass substrate in this order. Notably, the anode 2 (e.g., the ITO electrode) and the cathode 8 (e.g., the Al—Li electrode) are connected together via a power source.

Driving

The organic electroluminescence device can emit light when a DC voltage (which, if necessary, contains AC components) (generally 2 volts to 15 volts) or a DC is applied to between the anode and the cathode.

The organic electroluminescence device can be applied to an active matrix using a thin film transistor (TFT). An active layer of the thin film transistor may be made from, for example, amorphous silicon, high-temperature polysilicon, low-temperature polysilicon, microcrystalline silicon, oxide semiconductor, organic semiconductor and carbon nanotube.

The thin film transistor used for the organic electroluminescence device may be those described in, for example, International Publication No. WO2005/088726, JP-A No. 2006-165529 and U.S. Patent Application Publication No. 2008/0237598 A1.

The organic electroluminescence device is not particularly limited. In the organic electroluminescence device, the light-extraction efficiency can be further improved by various known methods. It is possible to increase the light-extraction efficiency to improve the external quantum efficiency, for example, by processing the surface profile of the substrate (for example, by forming a fine concavo-convex pattern), by controlling the refractive index of the substrate, the ITO layer and/or the organic layer, or by controlling the thickness of the substrate, the ITO layer and/or the organic layer.

The manner in which light is extracted from the organic electroluminescence device may be top-emission or bottom-emission.

The organic electroluminescence device may have a resonator structure. For example, on a transparent substrate are stacked a multi-layered film mirror composed of a plurality of laminated films having different refractive indices, a transparent or semi-transparent electrode, a light-emitting layer and a metal electrode. The light generated in the light-emitting layer is repeatedly reflected between the multi-layered film mirror and the metal electrode (which serve as reflection plates); i.e., is resonated.

In another preferred embodiment, a transparent or semi-transparent electrode and a metal electrode are stacked on a transparent substrate. In this structure, the light generated in the emission layer is repeatedly reflected between the transparent or semi-transparent electrode and the metal electrode (which serve as reflection plates); i.e., is resonated.

For forming the resonance structure, an optical path length determined based on the effective refractive index of two reflection plates, and on the refractive index and the thickness of each of the layers between the reflection plates is adjusted to be an optimal value for obtaining a desired resonance wavelength. The calculation formula applied in the case of the first embodiment is described in JP-A No. 09-180883. The calculation formula in the case of the second embodiment is described in JP-A No. 2004-127795.

Application

The application of the organic electroluminescence device is not particularly limited and may be appropriately selected depending on the intended purpose. The organic electroluminescence device can be suitably used in, for example, display devices, displays, backlights, electrophotography, illuminating light sources, recording light sources, exposing light sources, reading light sources, markers, signboards, interior accessories and optical communication.

As a method for forming a full color-type display, there are known, for example, as described in "Monthly Display," September 2000, pp. 33 to 37, a tricolor light emission method by arranging, on a substrate, organic electroluminescence devices corresponding to three primary colors (blue color (B), green color (G) and red color (R)); a white color method by separating white light emitted from an organic electroluminescence device for white color emission into three primary colors through a color filter; and a color conversion method by converting a blue light emitted from an organic electroluminescence device for blue light emission into red color (R) and green color (G) through a fluorescent dye layer. Further, by combining a plurality of organic electroluminescence devices emitting lights of different colors which are obtained by the above-described methods, plane-type light sources emitting lights of desired colors can be obtained. For example, there are exemplified white light-emitting sources obtained by combining blue and yellow light-emitting devices, and white light-emitting sources obtained by combining blue, green and red light-emitting devices.

EXAMPLES

The present invention will next be described by way of Examples, which should not be construed as limiting the present invention thereto.

Notably, in Examples and Comparative Examples, unless otherwise specified, the vapor deposition rate was 0.2 nm/sec. The vapor deposition rate was measured with a quartz crystal unit. Also, the layer thicknesses given below were measured with a quartz crystal unit. The melting temperature of each compound was measured with the below-described method. The boiling point of each solvent is cited from its MSDS (Material Safety Data Sheet).

<Measurement Method for Melting Temperature>
A hot stage (MT-350, product of Collet Kogyo Co., Ltd.) and a polarization microscope (ECLIPSE50iPOL, product of Nikon Corporation) were used to measure the temperature at which powder melted.

Example 1

Production of Organic Electroluminescence Device

A glass substrate (thickness: 0.7 mm, 25 mm×25 mm) was placed in a washing container. The glass substrate was washed in 2-propanol through ultrasonication, and then was UV-ozone treated for 30 min. The following layers were formed on this glass substrate.

First, ITO (Indium Tin Oxide) was vapor-deposited through sputtering on the glass substrate so as to form a 150 nm-thick anode. The obtained transparent supporting substrate was etched and washed.

Next, the anode (ITO) was coated through spin coating with a coating liquid which had been prepared by dissolving or dispersing 2 parts by mass of arylamine derivative (trade name: PTPDES-2, product of CHEMIPRO KASEI KAISHA, LTD., Tg=205° C.) in 98 parts by mass of cyclohexanone for electronics industry (product of KANTO KAGAKU). The resultant product was dried at 120° C. for 30 min and then annealed at 160° C. for 10 min, to thereby form a hole injection layer having a thickness of 40 nm.

Separately, a hole transport layer-coating liquid was prepared by dissolving or dispersing, in 2,000 parts by mass of xylene for electronics industry (product of KANTO KAGAKU), 19 parts by mass of a compound (arylamine derivative) represented by the following Structural Formula (6) (weight average molecular weight Mw=8,000 (calculated through GPC (gel permeation chromatograph) on the basis of standard polystyrene)) and 1 part by mass of a compound expressed by the following Structural Formula (7), followed by stirring for 1 hour. Then, the hole injection layer was coated through spin coating with the hole transport layer-coating liquid. The obtained product was dried at 120° C. for 30 min and then annealed at 150° C. for 10 min, to thereby form a hole transport layer having a thickness of 15 nm. Notably, the spin coating for forming the hole injection layer or the hole transport layer was performed in a glove box (dew point: −70° C., oxygen concentration: 8 ppm). The contact angle of the hole transport layer with respect to pure water was measured by the below-described method and was found to be 80°.

Structural Formula (6)

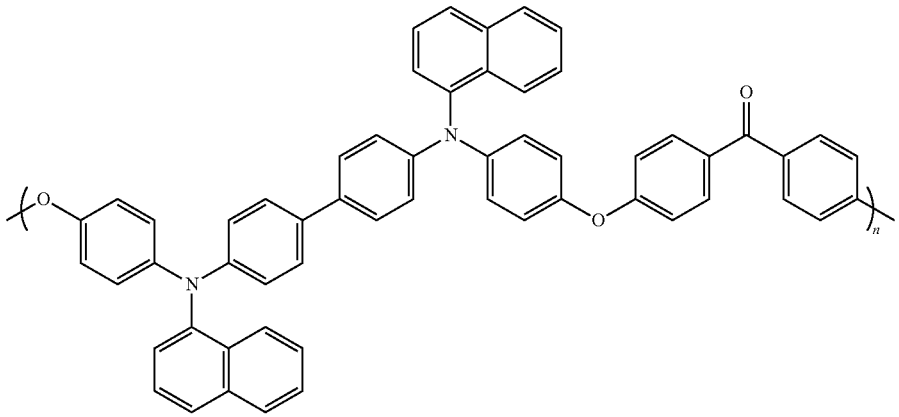

Where, n is an integer.

Structural Formula (7)

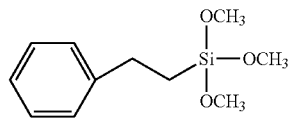

<Measurement Method for Contact Angle>
Using a contact angle meter (Drop Master 300, product of Kyowa Interface Science Co., LTD.), 2 μL of pure water was dropped on the hole transport layer and the contact angle therebetween was measured. Notably, the contact angle was represented by an average of the contact angles at 10 locations.

Separately, 4.75 parts by mass of a compound expressed by the following Structural Formula (1) (melting temperature: 125° C.) serving as a host material and 0.25 parts by mass of a compound expressed by the following Structural Formula (5) (trade name: Ir(ppy)$_3$, product of CHEMIPRO KASEI KAISHA, LTD.) serving as a phosphorescent light-emitting material were dissolved or dispersed in 995 parts by mass of methyl isobutyl ketone (boiling point: 116° C., product of Wako Pure Chemical Industries, Ltd.). Then, molecular sieve (trade name: molecular sieve 4A 1/16, product of Wako Pure Chemical Industries, Ltd.) was added to the resultant mixture, followed by filtration with a syringe filter having a pore size of 0.22 μm in the glove box, to thereby prepare a light-emitting layer-coating liquid. The prepared light-emitting layer-coating liquid was applied to the above-formed hole transport layer through spray coating. The obtained product was dried at 120° C. for 30 min and then annealed at 160° C. for 10 min, to thereby form a light-emitting layer having a thickness of 30 nm. The contact angle of the light-emitting layer with respect to pure water was measured by the above-described method and was found to be 89°. The light-emitting layer was observed under a microscope (trade name: Wyco NT1100, product of Veeco Instruments Inc.). As a result, no voids were observed and a uniform surface could be formed.

Structural Formula (5)

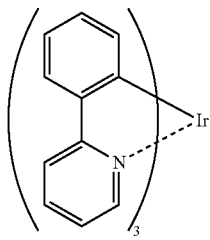

Next, BAlq (bis-(2-methyl-8-quinolinolato)-4-(phenyl-phenolate)-aluminium-(III)) was deposited on the light-emitting layer by a vacuum vapor deposition method, to thereby form an electron transport layer having a thickness of 40 nm.

Next, lithium fluoride (LiF) was vapor-deposited on the electron transport layer to form an electron injection layer having a thickness of 1 nm.

Next, metal aluminum was vapor-deposited on the electron injection layer to form a cathode having a thickness of 70 nm.

The thus-obtained laminate was placed in a glove box which had been purged with argon gas, and then was sealed in a stainless steel sealing can using a UV-ray curable adhesive (XNR5516HV, product of Nagase-CIBA Ltd.), whereby an organic electroluminescence device was produced. Then, a DC voltage of 12 V was applied to the produced organic electroluminescence device for electrical conduction. As a result, there were no dark spots and a uniform light-emitting surface was confirmed. Here, the "dark spots" are regions where light is not emitted.

Notably, the compound expressed by the above Structural Formula (1) was synthesized according to the following synthesis schemes 1 and 2.

Structural Formula (1)

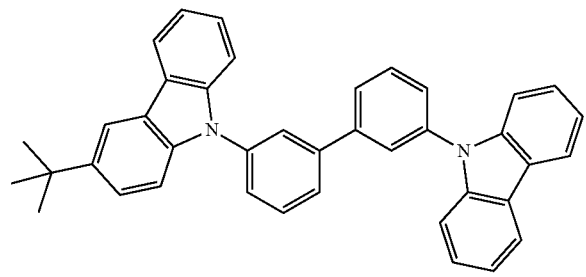

<Synthesis scheme 1>

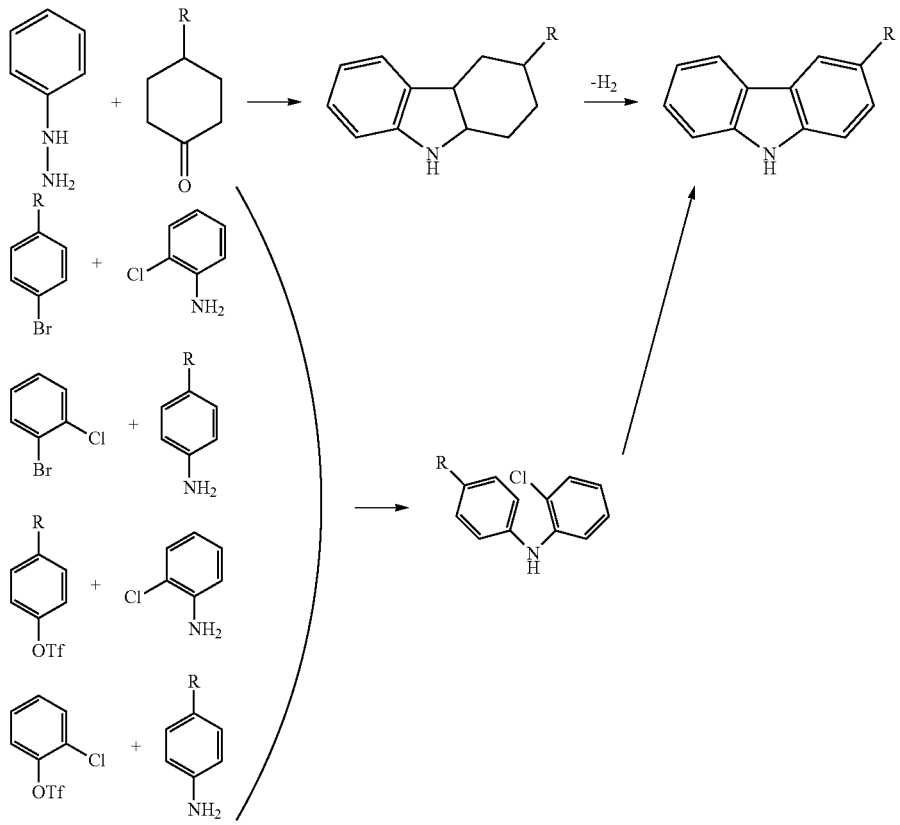

33

<Synthesis scheme 2>

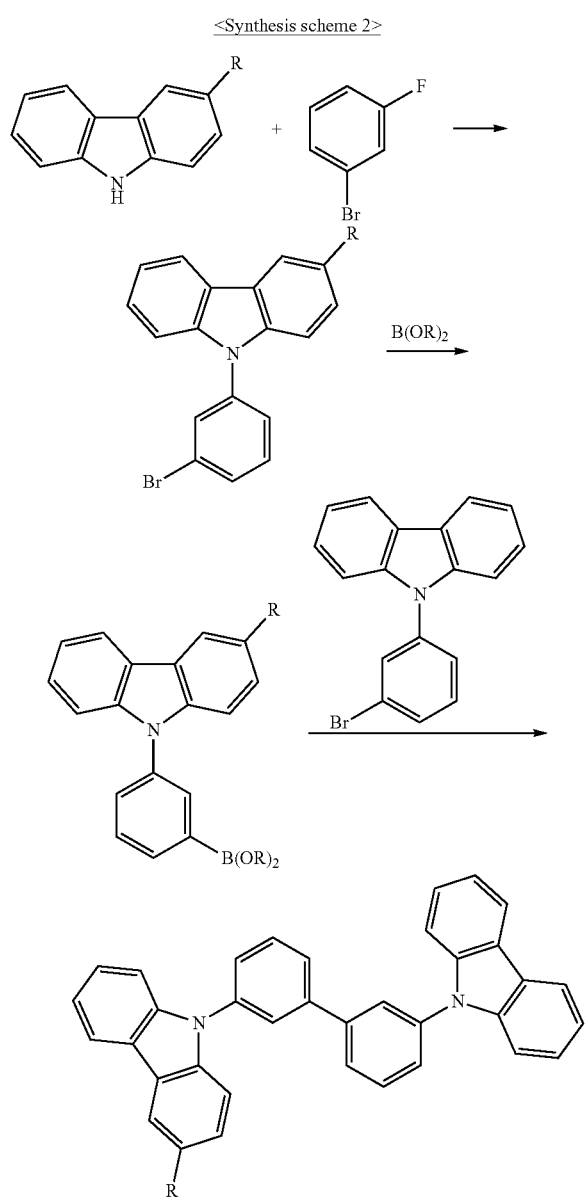

Example 2

An organic electroluminescence device was produced in the same manner as in Example 1, except that the conditions for the formation of the light-emitting layer were changed as follows: the host material was changed from the compound expressed by the above Structural Formula (1) to a compound expressed by the following Structural Formula (2) (melting temperature: 128° C.); the solvent was changed from methyl isobutyl ketone to a solvent mixture (mixing ratio: 2/8) of xylene for electronics industry (boiling point: 144° C., product of KANTO KAGAKU) and anhydrous toluene (boiling point: 110° C., product of Wako Pure Chemical Industries, Ltd.); and the process of drying at 120° C. for 30 min and annealing at 160° C. for 10 min was changed to a process of drying at 125° C. and 30 min and annealing at 160° C. and 10 min. Similar to Example 1, the contact angle of the light-emitting layer with respect to pure water was measured by the above-described method and was found to be 87.6°. The light-emitting layer was observed under a microscope (trade name: Wyco NT1100, product of Veeco Instruments Inc.). As a result, no voids were observed and a uniform surface could be formed.

Also, a DC voltage of 12 V was applied to the produced organic electroluminescence device for electrical conduction. As a result, there were no dark spots and a uniform light-emitting surface was confirmed.

Structural Formula (2)

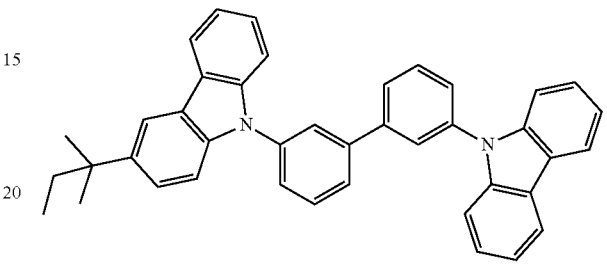

Notably, the compound expressed by the above Structural Formula (2) was synthesized according to the above synthesis schemes 1 and 2.

Example 3

An organic electroluminescence device was produced in the same manner as in Example 1, except that the conditions for the formation of the light-emitting layer were changed as follows: the host material was changed from the compound expressed by the above Structural Formula (1) to a compound expressed by the following Structural Formula (3) (melting temperature: 155° C.); and the process of drying at 120° C. for 30 min and annealing at 160° C. for 10 min was changed to a process of drying at 120° C. and 30 min and annealing at 165° C. and 10 min. The contact angle of the light-emitting layer with respect to pure water was measured by the above-described method and was found to be 89°. The light-emitting layer was observed under a microscope (trade name: Wyco NT1100, product of Veeco Instruments Inc.). As a result, no voids were observed and a uniform surface could be formed.

Also, a DC voltage of 12 V was applied to the produced organic electroluminescence device for electrical conduction. As a result, there were no dark spots and a uniform light-emitting surface was confirmed.

Structural Formula (3)

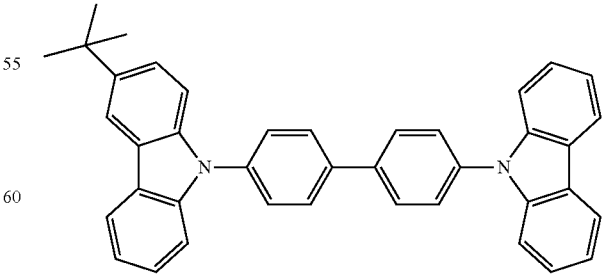

The compound expressed by the above Structural Formula (3) was synthesized according to the above synthesis scheme 1 and the following synthesis scheme 3.

<Synthesis scheme 3>

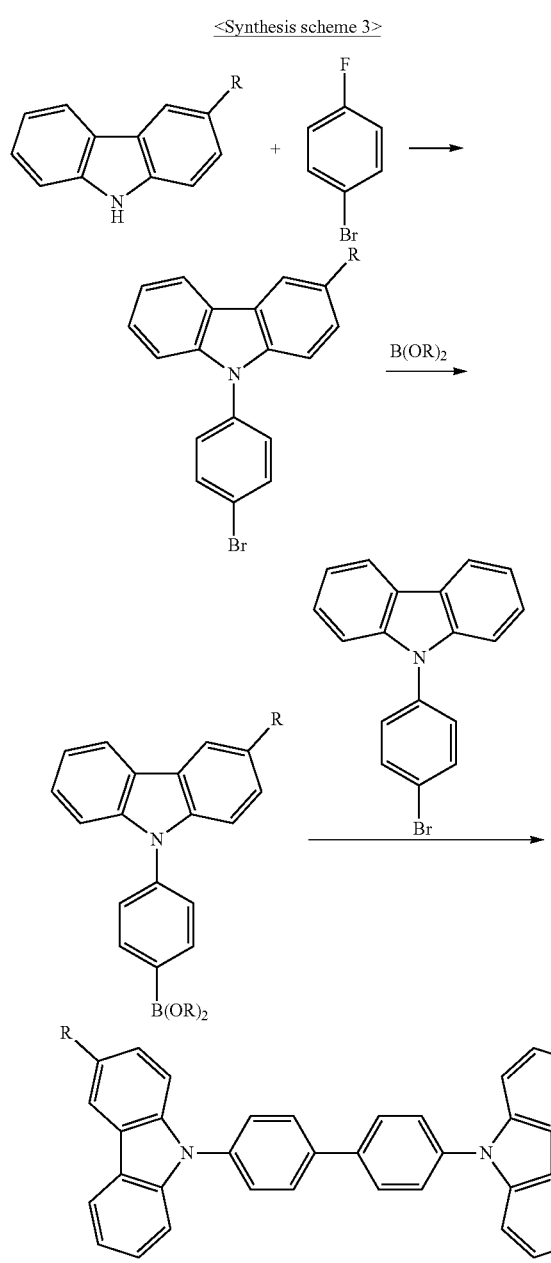

Example 4

Production of Organic Electroluminescence Device

A glass substrate (thickness: 0.7 mm, 25 mm×25 mm) was placed in a washing container. The glass substrate was washed in 2-propanol through ultrasonication, and then was UV-ozone treated for 30 min. The following layers were formed on this glass substrate. First, ITO (Indium Tin Oxide) was vapor-deposited through sputtering on the glass substrate so as to form a 150 nm-thick anode. The obtained transparent supporting substrate was etched and washed.

Next, in a glove box (dew point: −70° C., oxygen concentration: 8 ppm), the anode (ITO) was coated through spin coating with a coating liquid which had been prepared by dissolving or dispersing 2 parts by mass of arylamine derivative (trade name: PTPDES-2, product of CHEMIPRO KASEI KAISHA, LTD., Tg=205° C.) in 98 parts by mass of cyclohexanone for electronics industry (product of KANTO KAGAKU). The resultant product was dried at 120° C. for 30 min and then annealed at 160° C. for 10 min, to thereby form a hole injection layer having a thickness of 40 nm.

The contact angle of the hole injection layer with respect to pure water was measured by the above-described method and was found to be 78.4°.

Separately, 4.75 parts by mass of a compound expressed by the following Structural Formula (4) (melting temperature: 170° C.) serving as a host material and 0.25 parts by mass of a compound expressed by the following Structural Formula (5) (trade name: Ir(ppy)$_3$, product of CHEMIPRO KASEI KAISHA, LTD.) serving as a phosphorescent light-emitting material were dissolved or dispersed in 995 parts by mass of methyl isobutyl ketone (boiling point: 116° C., product of Wako Pure Chemical Industries, Ltd.). Then, molecular sieve (trade name: molecular sieve 4A 1/16, product of Wako Pure Chemical Industries, Ltd.) was added to the resultant mixture, followed by filtration with a syringe filter having a pore size of 0.22 μm in the glove box, to thereby prepare a light-emitting layer-coating liquid. The prepared light-emitting layer-coating liquid was applied to the above-formed hole transport layer through spray coating. The obtained product was dried at 120° C. for 30 min and then annealed at 190° C. for 5 min, to thereby form a light-emitting layer having a thickness of 40 nm. The contact angle of the light-emitting layer with respect to pure water was measured by the above-described method and was found to be 73.2°. The light-emitting layer was observed under a microscope (trade name: Wyco NT1100, product of Veeco Instruments Inc.). As a result, no voids were observed and a uniform surface could be formed.

Structural Formula (4)

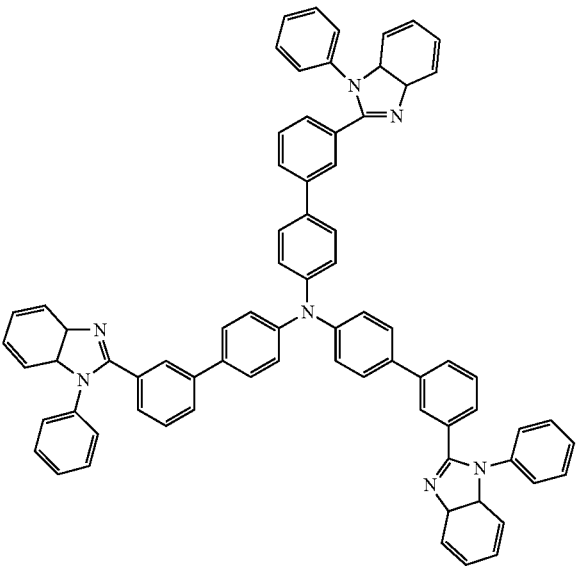

Notably, the compound expressed by the above Structural Formula (4) was synthesized according to the method described in JP-A No. 2007-269772.

Next, BAlq (bis-(2-methyl-8-quinolinolato)-4-(phenyl-phenolate)-aluminium-(III)) was deposited on the light-emitting layer by a vacuum vapor deposition method, to thereby form an electron transport layer having a thickness of 40 nm.

Next, lithium fluoride (LiF) was vapor-deposited on the electron transport layer to form an electron injection layer having a thickness of 1 nm.

Next, metal aluminum was vapor-deposited on the electron injection layer to form a cathode having a thickness of 70 nm.

The thus-obtained laminate was placed in a glove box which had been purged with argon gas, and then was sealed in a stainless steel sealing can using a UV-ray curable adhesive (XNR5516HV, product of Nagase-CIBA Ltd.), whereby an organic electroluminescence device was produced. Then, a DC voltage of 12 V was applied to the produced organic electroluminescence device for electrical conduction. As a result, there were no dark spots and a uniform light-emitting surface was confirmed.

Example 5

An organic electroluminescence device was produced in the same manner as in Example 1, except that the hole transport layer was not formed and the light-emitting layer was formed on the hole injection layer.

The contact angle of the hole injection layer with respect to pure water was measured by the above-described method and was found to be 78.4°. The contact angle of the light-emitting layer with respect to pure water was measured by the above-described method and was found to be 89°. The light-emitting layer was observed under a microscope (trade name: Wyco NT1100, product of Veeco Instruments Inc.). As a result, no voids were observed and a uniform surface could be formed. Furthermore, a DC voltage of 12 V was applied to the produced organic electroluminescence device for electrical conduction. As a result, there were no dark spots and a uniform light-emitting surface was confirmed.

Comparative Example 1

An organic electroluminescence device was produced in the same manner as in Example 1, except that the annealing at 160° C. for 10 min was not performed in the formation of the light-emitting layer.

The contact angle of the hole injection layer with respect to pure water was measured by the above-described method and was found to be 80°. The contact angle of the light-emitting layer with respect to pure water was measured by the above-described method and was found to be 89°. The light-emitting layer was observed under a microscope (trade name: Wyco NT1100, product of Veeco Instruments Inc.). As a result, voids and irregularities were observed. Furthermore, a DC voltage of 12 V was applied to the produced organic electroluminescence device for electrical conduction. As a result, there were light spots and a non-uniform light-emitting surface was confirmed.

Comparative Example 2

Production of Organic Electroluminescence Device

A glass substrate (thickness: 0.7 mm, 25 mm×25 mm) was placed in a washing container. The glass substrate was washed in 2-propanol through ultrasonication, and then was UV-ozone treated for 30 min. The following layers were formed on this glass substrate. First, ITO (Indium Tin Oxide) was vapor-deposited through sputtering on the glass substrate so as to form a 150 nm-thick anode. The obtained transparent supporting substrate was etched and washed.

Next, the anode (ITO) was coated through spin coating with a coating liquid which had been prepared by dissolving or dispersing 90 parts by mass of polyethylenedioxythiophene (PEDOT)/polystyrene sulfonic acid (PSS) (trade name: CLEVIOS P AI4083, product of H.C. Sterck, Tg=190° C.) in 10 parts by mass of ethanol (product of KANTO KAGAKU). The resultant product was dried at 100° C. for 10 min and then dried in vacuum at 160° C. for 120 min, to thereby form a hole injection layer having a thickness of 40 nm.

The contact angle of the hole injection layer with respect to pure water was measured by the above-described method and was found to be 12.4°.

Separately, 4.75 parts by mass of a compound expressed by the above Structural Formula (1) (melting temperature: 125° C.) serving as a host material and 0.25 parts by mass of a compound expressed by the above Structural Formula (5) (trade name: Ir(ppy)$_3$, product of CHEMIPRO KASEI KAISHA, LTD.) serving as a phosphorescent light-emitting material were dissolved or dispersed in 995 parts by mass of methyl isobutyl ketone (boiling point: 116° C., product of Wako Pure Chemical Industries, Ltd.). Then, molecular sieve (trade name: molecular sieve 4A 1/16, product of NACALAI TESQUE, INC.) was added to the resultant mixture, followed by filtration with a syringe filter having a pore size of 0.22 µm in the glove box, to thereby prepare a light-emitting layer-coating liquid. The prepared light-emitting layer-coating liquid was applied to the above-formed hole injection layer through spray coating. The obtained product was dried at 120° C. for 30 min and then annealed at 160° C. for 10 min, to thereby form a light-emitting layer having a thickness of 35 nm. The contact angle of the light-emitting layer with respect to pure water was measured by the above-described method and was found to be 89°. The light-emitting layer was observed under a microscope (trade name: Wyco NT1100, product of Veeco Instruments Inc.). As a result, numerous small voids were observed.

Structural Formula (1)

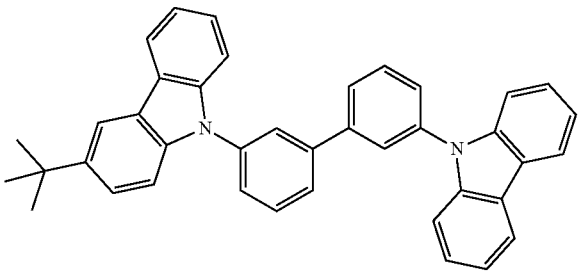

Structural Formula (5)

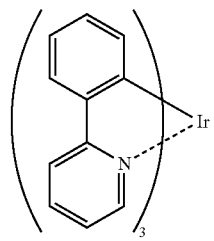

Next, BAlq (bis-(2-methyl-8-quinolinolato)-4-(phenylphenolate)-aluminium-(III)) was deposited on the light-emitting layer by a vacuum vapor deposition method, to thereby form an electron transport layer having a thickness of 40 nm.

Next, lithium fluoride (LiF) was vapor-deposited on the electron transport layer to form an electron injection layer having a thickness of 1 nm.

Next, metal aluminum was vapor-deposited on the electron injection layer to form a cathode having a thickness of 70 nm.

The thus-obtained laminate was placed in a glove box which had been purged with argon gas, and then was sealed in a stainless steel sealing can using a UV-ray curable adhesive (XNR5516HV, product of Nagase-CIBA Ltd.), whereby an organic electroluminescence device was produced. Then, a DC voltage of 12 V was applied to the produced organic electroluminescence device for electrical conduction. As a result, there were dark spots and a non-uniform light-emitting surface was confirmed.

Comparative Example 3

An organic electroluminescence device was produced in the same manner as in Comparative Example 2, except that the procedure including: performing spin-coating of the coating liquid prepared by dissolving or dispersing 90 parts by mass of polyethylenedioxythiophene (PEDOT)/polystyrene sulfonic acid (PSS) in 10 parts by mass of ethanol; performing drying at 100° C. for 10 min; and performing drying in vacuum at 160° C. for 120 min to thereby form a hole injection layer having a thickness of 40 nm was changed to a procedure including: performing spin-coating of a coating liquid prepared in the following manner; and performing drying at 120° C. for 30 min to thereby form a hole injection layer having a thickness of 40 nm.

Preparation of Hole Injection Layer-Coating Liquid

Sixty grams of an aqueous colloidal dispersion liquid (5.0% by mass) of NAFION (registered trademark) (DE520), 240 g of deionized water and 1.0 g of sodium persulfate were weighed and placed in a 500-mL separable flask, and the resultant mixture was stirred for 1 hour under $N_2$ flow. Next, 350 µg of iron(III) sulfate n-hydrate (product of Wako Pure Chemical Industries, Ltd., 091-02832) was added to the mixture. In addition, 1.5 g of 3,4-ethylenedioxythiophene was added thereto, followed by stirring for 4 hours.

Thereafter, 10 g of ion exchange resin LEWATIT (registered trademark) S100 and 10 g of ion exchange resin LEWATIT (registered trademark) MP62WS were added to the reaction mixture, followed by stirring for 1 hour to terminate the reaction. Before use, these two ion exchange resins were individually washed with deionized water until the wash water became colorless.

The ion exchange resins were separated through filtration to obtain an aqueous dispersion liquid of PEDOT (poly(3,4-ethylenedioxythiophene))/NAFION.

Next, 1N hydrochloric acid was added to the obtained aqueous dispersion liquid. The resultant mixture was centrifugated and then the solid matter was recovered. Deionized water was added to the solid matter and then the resultant mixture was centrifugated, to thereby obtain a slurry containing poly(3,4-ethylenedioxythiophene) (PEDOT)/NAFION.

This slurry was mixed with a solvent (9:1 solvent mixture of isopropanol and ethylene glycol) to thereby prepare a hole injection layer-coating liquid having a solid content of 20% by mass.

The contact angle of the hole injection layer with respect to pure water was measured by the above-described method and was found to be 119°. When the light-emitting layer was formed, the light-emitting layer was peeled off from the hole injection layer to be in the form of particles. The contact angle of the light-emitting layer with respect to pure water was measured by the above-described method and was found to be 89°. Furthermore, a DC voltage of 12 V was applied to the produced organic electroluminescence device for electrical conduction. As a result, light emission could not be confirmed.

Comparative Example 4

An organic electroluminescence device was produced in the same manner as in Comparative Example 2, except that the procedure including: performing spin-coating of the coating liquid prepared by dissolving or dispersing 90 parts by mass of polyethylenedioxythiophene (PEDOT)/polystyrene sulfonic acid (PSS) in 10 parts by mass of ethanol; performing drying at 100° C. for 10 min; and performing drying in vacuum at 160° C. for 120 min to thereby form a hole injection layer having a thickness of 40 nm was changed to vapor-depositing $MoO_3$ to form a hole injection layer having a thickness of 20 nm.

The contact angle of the hole injection layer with respect to pure water was measured by the above-described method and was found to be 60°. The light-emitting layer was observed under a microscope (trade name: Wyco NT1100, product of Veeco Instruments Inc.). As a result, numerous small voids were observed. The contact angle of the light-emitting layer with respect to pure water was measured by the above-described method and was found to be 89°. Furthermore, a DC voltage of 12 V was applied to the produced organic electroluminescence device for electrical conduction. As a result, there were dark spots and a non-uniform light-emitting surface was confirmed.

Comparative Example 5

An organic electroluminescence device was produced in the same manner as in Comparative Example 4, except that the materials of the light-emitting layer-coating liquid were changed to the materials of the light-emitting layer-coating liquid in Example 4.

The contact angle of the hole injection layer with respect to pure water was measured by the above-described method and was found to be 60°. The light-emitting layer was observed under a microscope (trade name: Wyco NT1100, product of Veeco Instruments Inc.). As a result, numerous small voids were observed. The contact angle of the light-emitting layer with respect to pure water was measured by the above-described method and was found to be 73.2°. Furthermore, a DC voltage of 12 V was applied to the produced organic electroluminescence device for electrical conduction. As a result, there were dark spots and a non-uniform light-emitting surface was confirmed.

<Measurement of Ra Value>

Next, each of the produced organic electroluminescence devices of Examples 1 to 5 and Comparative Examples 1 to 5 was measured by the below-described methods for the Ra values of the light-emitting layer before and after the host material in the light-emitting layer melts. The measurement results are shown in Table 1.

Notably, the light-emitting layer before the host material in the light-emitting layer melts means the light-emitting layer at the time when the heating was performed at a temperature lower than the melting temperature of the host material but higher than the boiling point of the solvent, and the light-emitting layer after the host material in the light-emitting layer melts means the light-emitting layer at the time when the heating was performed at a temperature higher than the melting temperature of the host material.

Measuring Methods for the Ra Values of the Light-Emitting Layer Before and after the Host Material Melts A microscope (trade name: Wyco NT1100, product of Veeco Instruments Inc.) was used to measure the Ra of a region of 2.5 mm×1.8 mm (i.e., observation area).

The Ra values of the light-emitting layer before and after the host material in the light-emitting layer melts were measured in the following manner.

Measuring Method for the Ra Value of the Light-Emitting Layer Before the Host Material in the Light-Emitting Layer Melts The light-emitting layer was coated and heated for drying, and the resultant light-emitting layer was measured for the Ra.

Measuring Method for the Ra Value of the Light-Emitting Layer after the Host Material in the Light-Emitting Layer Melts The light-emitting layer was coated and heated for drying and annealing, and the resultant light-emitting layer was measured for the Ra.

TABLE 1

|  | Adjacent layer | Light-emitting layer | Difference as an absolute value between | Ra value before | Ra value after | | |
|---|---|---|---|---|---|---|---|
|  | Materials | Contact angle (°) | Contact angle (°) | contact angles (°) | melting (nm) | melting (nm) | Results | Remarks |
| Ex. 1 | Structural Formula (6) | 80 | 89 | 9.0 | 6.5 | 0.35 | Uniform light emission | |
| Ex. 2 | Structural Formula (6) | 80 | 87.6 | 7.6 | 6.9 | 0.38 | Uniform light emission | |
| Ex. 3 | Structural Formula (6) | 80 | 89 | 9.0 | 8.1 | 0.85 | Uniform light emission | |
| Ex. 4 | PTPDES-2 | 78.4 | 73.2 | 5.2 | 7.3 | 0.78 | Uniform light emission | |
| Ex. 5 | PTPDES-2 | 78.4 | 89 | 10.6 | 6.5 | 0.54 | Uniform light emission | |
| Comp. Ex. 1 | Structural Formula (6) | 80 | 89 | 9.0 | 6.5 | 6.5 | Defects present | No annealing |
| Comp. Ex. 2 | PEDOT/PSS | 12.4 | 89 | 76.6 | 5.8 | 2.8 | Defects present | |
| Comp. Ex. 3 | PEDOT/NAFION | 119 | 89 | 30.0 | 7.8 | Not evaluated | No light emission | |
| Comp. Ex. 4 | $MoO_3$ | 60 | 89 | 29.0 | 9.0 | >10 | Defects present | |
| Comp. Ex. 5 | $MoO_3$ | 60 | 73.2 | 13.2 | 8.5 | >10 | Defects present | |

In Table 1, "Uniform light emission" means that the light-emitting surface emitted light without dark sports or light spots, "Defects present" means that dark spots were formed, and "No light emission" means that light was not emitted even by electrical conduction.

The organic electroluminescence devices of Examples 1 to 5, each containing the light-emitting layer formed by heating at a temperature higher than the melting temperature of the host material and higher than the boiling point of the solvent where the difference as an absolute value between the contact angle A (°) of the formed light-emitting layer with respect to pure water and the contact angle B (°) of the adjacent layer with respect to pure water was 13 (°) or smaller, were found to be improved in surface uniformity of their light-emitting layer (i.e., they were found to realize uniform light emission) as compared with the organic electroluminescence devices of Comparative Examples 1 to 5.

INDUSTRIAL APPLICABILITY

The organic electroluminescence device produced by the method of the present invention for producing an organic electroluminescence device can attain excellent light-emission efficiency and long light-emission time, and thus, can be suitably used in, for example, display devices, displays, backlights, electrophotography, illuminating light sources, recording light sources, exposing light sources, reading light sources, markers, signboards, interior accessories and optical communication.

REFERENCE SINGS LIST

1 Substrate
2 Anode
3 Hole injection layer
4 Hole transport layer
5 Light-emitting layer
6 Electron transport layer
7 Electron injection layer
8 Cathode
10 Organic electroluminescence device

The invention claimed is:
1. A method for producing an organic electroluminescence device which contains an anode, a cathode and an organic layer between the anode and the cathode where the organic layer contains a light-emitting layer and an adjacent layer adjacent to the light-emitting layer, the method comprising:

applying to the adjacent layer a coating liquid prepared by dissolving or dispersing a light-emitting material and a host material in a solvent, heating the coating liquid applied to the adjacent layer at a temperature equal to or above the boiling point of the solvent but lower than the melting temperature of the host material until the coating liquid dries, and after the coating liquid has dried, subsequently heating the coated adjacent layer at a temperature higher than the melting temperature of the host material to thereby form the light-emitting layer, wherein a difference as an absolute value between contact angle A (°) of the light-emitting layer with respect to pure water and contact angle B (°) of the adjacent layer with respect to pure water is 13 (°) or smaller, and wherein the host material is a compound expressed by any one of the following Structural Formulas (1) to (4):

Structural Formula (1)

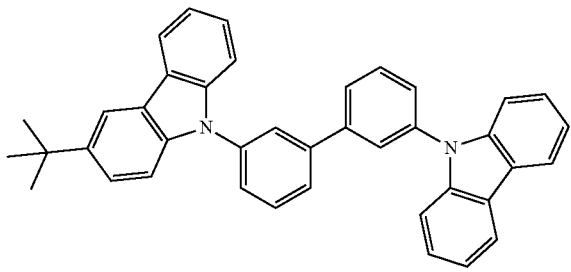

Structural Formula (2)

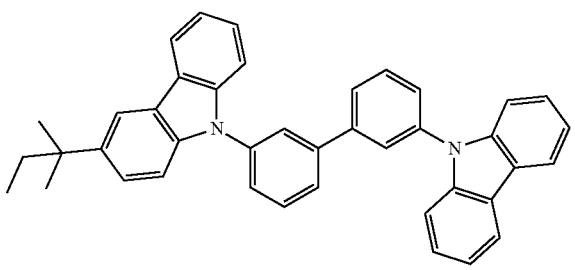

Structural Formula (3)

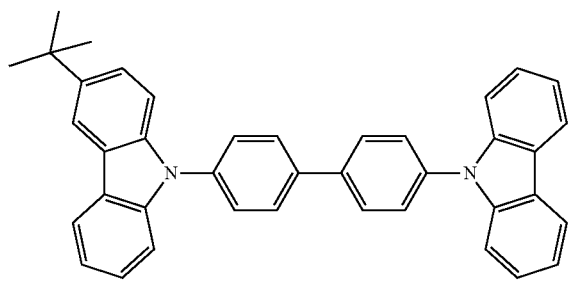

Structural Formula (4)

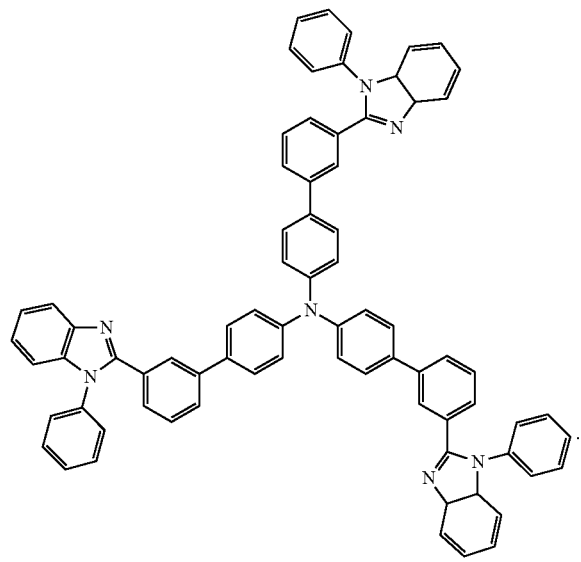

2. The method for producing an organic electroluminescence device according to claim 1, wherein the light-emitting material has a molecular weight of 1,500 or lower and the host material has a molecular weight of 1,500 or lower.

3. The method for producing an organic electroluminescence device according to claim 1, wherein the host material is a compound represented by the following General Formula (1) or (2):

General Formula (1)

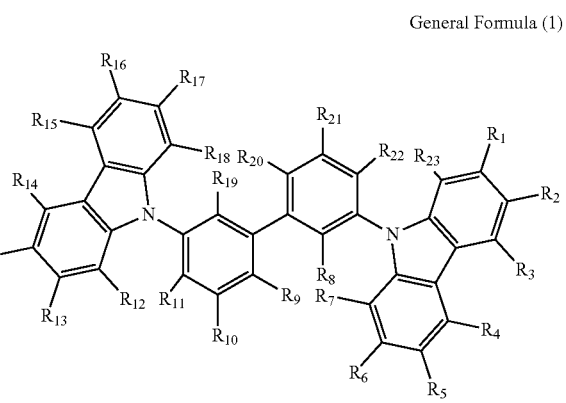

where R represents a t-butyl group, a t-amyl group, a trimethylsilyl group, a triphenylsilyl group or a phenyl group, and $R_1$ to $R_{23}$ each represent a hydrogen atom, a C1-C5 alkyl group, a cyano group, a fluorine atom, a trifluoro group, a trimethylsilyl group, a triphenylsilyl group or a phenyl group, General Formula (2)

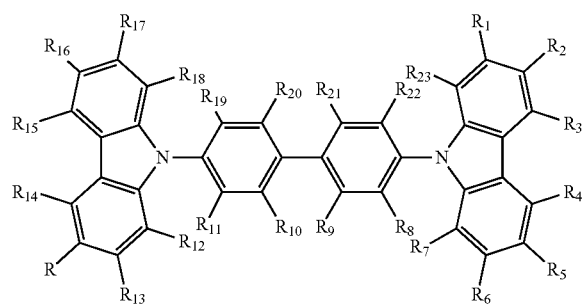

where R represents a t-butyl group, a t-amyl group, a trimethylsilyl group, a triphenylsilyl group or a phenyl group, and $R_1$ to $R_{23}$ each represent a hydrogen atom, a C1-C5 alkyl group, a cyano group, a fluorine atom, a trifluoro group, a trimethylsilyl group, a triphenylsilyl group or a phenyl group.

4. The method for producing an organic electroluminescence device according to claim 1, wherein the solvent contains at least one selected from the group consisting of aromatic hydrocarbons and ketones each having a boiling point of 100° C. or higher.

5. The method for producing an organic electroluminescence device according to claim 1, wherein the temperature of the heating of the coated adjacent layer is higher than the melting temperature of the host material by 20° C. or higher.

6. The method for producing an organic electroluminescence device according to claim 1, wherein the light-emitting layer has an Ra value of 5 nm or more before the host material melts and the light-emitting layer has an Ra value of 1 nm or less after the host material melts.

* * * * *